(12) United States Patent
Dan

(10) Patent No.: US 7,905,836 B2
(45) Date of Patent: Mar. 15, 2011

(54) LOCALIZED PRODUCTION OF MICROBUBBLES AND CONTROL OF CAVITATIONAL AND HEATING EFFECTS BY USE OF ENHANCED ULTRASOUND

(75) Inventor: Adam Dan, Haifa (IL)

(73) Assignee: Technion Research and Development Foundation, Haifa (IL)

(*) Notice: Subject to any disclaimer, the term of this patent is extended or adjusted under 35 U.S.C. 154(b) by 311 days.

(21) Appl. No.: 10/587,295

(22) PCT Filed: Feb. 3, 2005

(86) PCT No.: PCT/IL2005/000128
§ 371 (c)(1),
(2), (4) Date: Jul. 25, 2006

(87) PCT Pub. No.: WO2005/074365
PCT Pub. Date: Aug. 18, 2005

(65) Prior Publication Data
US 2007/0161902 A1 Jul. 12, 2007

(51) Int. Cl.
*A61B 8/00* (2006.01)
(52) U.S. Cl. .............. 600/439; 600/437; 601/3
(58) Field of Classification Search .............. 601/2, 3–4; 600/458, 439
See application file for complete search history.

(56) References Cited

U.S. PATENT DOCUMENTS

| | | | |
|---|---|---|---|
| 4,618,831 A * | 10/1986 | Egami et al. ............ 330/124 R |
| 5,219,401 A * | 6/1993 | Cathignol et al. ............ 600/439 |
| 5,522,869 A | 6/1996 | Burdette et al. |
| 5,573,497 A | 11/1996 | Chapelon |
| 5,601,526 A | 2/1997 | Chapelon et al. |
| 5,675,554 A | 10/1997 | Cole et al. |
| 5,676,692 A | 10/1997 | Sanghvi et al. |
| 5,827,204 A * | 10/1998 | Grandia et al. ............ 601/2 |
| 6,413,216 B1 * | 7/2002 | Cain et al. ............ 600/439 |
| 6,508,774 B1 * | 1/2003 | Acker et al. ............ 601/2 |
| 6,551,244 B1 | 4/2003 | Gee |
| 2002/0009015 A1 * | 1/2002 | Laugharn et al. ............ 366/108 |
| 2004/0253183 A1 | 12/2004 | Uber, III et al. |

OTHER PUBLICATIONS

Bailey, M.R., et a., "Use of overpressure to assess the role of bubbles in focused ultrasound lesion shape in vitro" Ultrasound Med. Biol, vol. 27 No. 5, pp. 695-708 (2001).

Feng, R. et al.; "Enhancement of ultrasonic cavitation yield by multi-frequency sonication"; Ultrasonics Sonochemistry 9; pp. 231-236, 2002.

(Continued)

*Primary Examiner* — Tse Chen
*Assistant Examiner* — Joel F Brutus
(74) *Attorney, Agent, or Firm* — Holtz, Holtz, Goodman & Chick, PC

(57) ABSTRACT

A method of using ultrasound waves that are focused at a specific location in a medium is provided to cause localized production of bubbles at that location and to control the production, and the cavitational and heating effects that take place there. Production and control are accomplished by interference-specific waveforms at the focal point, which are not produced at other locations. Preferably, the region within the focal zone of all the transducers in which the specific waveform develops at significant intensities are very small. The method, and a system that performs the method, can be used to perform a variety of therapeutic procedures. Typical of such procedures is occlusion of varicose veins.

37 Claims, 17 Drawing Sheets

OTHER PUBLICATIONS

Holt, R. Glynn, et al., "Measurements of bubble-enhanced heating from focused, mhz-frequency ultrasound in a tissue-mimicking material", Ultrasound in Medicine & Biology. vol. 27, No. 10, pp. 1399-1412, 2001.

Sokka, S.D., "MRI-guided gas bubble enhanced ultrasound heating in in-vivo rabbit thigh"; Sokka, S.D., King, R., Hynynen, K., Phys. Med. Biol. 48, pp. 223-241 (2003).

Tasaki, K. et al., Division of Surgery, Chiba Cancer Center, Chiba, Japan. "Therapeutic Ultrasound", the proceedings of the 2nd International Symposium on Therapeutic Ultrasound (ITSU 2002).

Umemura et al.; "Enhancement of Sonodynamic Tissue Damage Production by Second-Harmonic Superimposition Theoretical Analysis and Its Mechanism"; IEEE Transactions on Ultrasonics, Ferroelectrics, and Frequency Control. vol. 43, No. 6; pp. 1054-1062; Nov. 1996.

Umemura et al.; "In vitro and in vivo enhancement of sonodynamically active cavitation by second-harmonic superimposition"; J. Acoust Soc, Am., vol. 101 No. 1, pp. 569-577; Jan. 1997.

Supplementary European Search Report dated Jun. 4, 2009 (7 pages), issued in counterpart European Application Serial No. 05703171.8.

Kaczkowski, et al., "High-intensity focused ultrasound (HIFU) array system for image-guided ablative therapy," Soc. Opt. Eng. USA, 2003, vol. 4954, pp. 209-219.

Fessenden et al., "Experience with a Multitransducer Ultrasound System for Localized Hyperthermia of Deep Tissues," IEEE Transactions on Biomedical Engineering, NJ, USA, Jan. 1, 1984, vol. BME-19, No. 1, pp. 126-135.

Gross et al., "A search for ultrasonic cavitation within the canine cardiovascular system," Ultrasound in Medicine and Biology, NY, USA, Jan. 1, 1985, vol. 11, No. 1, pp. 85-97.

* cited by examiner

LOCALIZED PRODUCTION OF MICROBUBBLES AND CONTROL OF CAVITATIONAL AND HEATING EFFECTS BY USE OF ENHANCED ULTRASOUND

This application is a U.S. National Phase Application under 35 USC 371 of International Application PCT/IL2005/000128 filed Feb. 3, 2005.

FIELD OF THE INVENTION

The present invention relates to the field of ultrasound technology. Specifically the invention relates to a system and methods for creating ultrasound waves and focusing them at a location and for controlling the waveform of the ultrasound to cause localized production of bubbles at the location and for control of the resultant cavitational effects or heating effects or a combination of the two effects, that take place in the focal region.

BACKGROUND OF THE INVENTION

The use of ultrasound for medical diagnostics and therapy is well known. Diagnostic techniques are based on the production and transmission of ultrasound waves into the body, and detection of the scattered echoes from the scanned region. Therapeutic methods are generally based on the use of focused beams of ultrasonic energy to produce high powered mechanical energy for disintegration of medical targets by heat or ablation caused by pressure waves. In body fluids such as blood or in the intercellular fluids in living tissue, the application of ultrasonic energy often leads to the creation of bubbles which grow in volume by a process known as rectified diffusion and eventually implode releasing large amounts of energy and generating sites of locally high temperature and pressure for very short periods of time.

Conventional ultrasound signals are generated by transducers powered to have a sinusoidal waveform such as that shown in FIG. 1. The horizontal axis represents time measured in μsec and the vertical axis the voltage applied to the transducer. When the applied electrical signal is in the frequency range of the transducer's frequency bandwidth and the signal is at least a few cycles long, the pressure wave generated by the transducer is of similar shape. The waves that are emitted from the transducer travel through the media as longitudinal waves (the transverse waves usually attenuate very rapidly and thus are ignored herein) having alternating compression and de-compression regions corresponding to the positive and negative portions of the waveform shown in FIG. 1. When the wave passes through a fluid, gases trapped inside dust motes or other particles in the fluid, or on the walls of the region containing the fluid will be drawn out from the fluid forming a small bubble. If the acoustic power density is small, then the bubble will oscillate around a relatively constant radius. This process is known as stable cavitation. If the power density is high, then gas diffuses into the bubble during the de-compression half-cycle of the sound waves and diffuses out from the bubble during the compression half-cycle. The rate of diffusion is proportional to the radius of the bubble and therefore the rate of diffusion into the bubble (which occurs when the bubble has expanded during the de-compression phase) exceeds that of the rate of diffusion out of the bubble (which occurs when the bubble has been compressed). The net result is that the radius of the bubble increases as the bubble oscillates. This process is known as rectified diffusion. Once the bubble's radius reaches a critical value, which depends on the power and frequency of the ultrasonic energy, it can no longer remain stable and the pressure caused by the next compression half-cycle will cause the bubble to implode, i.e. the fluids in the vicinity of the bubble oscillate with such an amplitude that the bubble breaks into small fractions.

In medical applications the energy released by the implosion of the bubbles in the rectified diffusion process is used to destroy near by cells. Various methods are known to produce cavitation at the desired location. For example, U.S. Pat. No. 5,219,401 teaches the use of relatively low power ultrasound energy to produce stable cavitation resulting in a population of bubbles at a site and then applying a second signal at another frequency and higher power to cause the bubbles to implode. U.S. Pat. No. 6,413,216 teaches the use of an unfocused transducer operating at a low frequency to create bubbles in a treatment area of a patient followed by the use of a focused ultrasound beam at a different frequency aimed at a specific region within the treatment area in order to cause cavitation and thereby create a lesion at a desired location. U.S. Pat. No. 5,827,204 teaches a method reported to produce large vaporous cavitation bubbles in a small confined area. The method comprises generating a low frequency signal having amplitude less than the cavitation threshold to produce a population of bubbles and superimposing on this signal a high frequency signal. The amplitude of the resulting modulated signal exceeds the cavitation threshold at the focus of the modulated beam.

Rapid hyperthermia resulting in tissue ablation or necrosis has proven to be a useful therapeutic modality, for example, in destroying cancerous tissue. Such applications are based on the use of high intensity focused beams of ultrasonic waves produced by either a single high power transducer or by focusing the energy from several transducers at the same location. Clinical application of high-intensity focused ultrasound (HIFU) is foreseen as the future non-invasive modality of choice, replacing the minimally invasive methods (RF ablation or Laser ablation). The ability to focus the ultrasound (US) energy at the specific location, with minimal absorption by neighboring tissue, by the tissue in between the transducer and that location, or by the tissue beyond that location—is the limiting factor of this technology.

At therapeutic intensities, the hyperthermia is often accompanied by bubble activity. In vitro and in vivo experiments alike have shown that under certain conditions bubble activity can give rise to a doubling of the heating rate (MRI-guided gas bubble enhanced ultrasound heating in in-vivo rabbit thigh, Sokka, S. D., King, R., Hynynen, K., Phys. Med. Biol. 48, pp. 223-241, 2003). Others have used cavitation suppression techniques to reduce the micro-bubble formation and make accurate ablation (Kentaro Tasaki, Takehide Asano, Kazuo Watanabe, Hiroshi Yamamoto, Division of Surgery, Chiba Cancer Center, Chiba, Japan. In "Therapeutic Ultrasound," the proceedings of the $2^{nd}$ International Symposium on Therapeutic Ultrasound (ISTU 2002). But more precisely, it was recently reported that a several times larger volume of tissue was coagulated with HIFU in a canine prostate with administration of Albunex Contrast Agent (CA) than without it. Kidneys were exposed to HIFU at 3.2 MHz in degassed saline, and when CA Optison was administered at a dose of 0.2 ml/kg, the temperature elevation induced by HIFU exposure was more than doubled. (The effect that tissue ultrasonic absorption will be doubled when contrast agent is added to the tissue at ~0.1 billion microbubbles/kg. was theoretically predicted, S Umemura, K Kawabata, K Sasaki, "Enhancement of sonodynamic tissue damage production by second-harmonic superposition: Theoretical analysis and its mechanisms", IEEE-TUFFC, Vol. 43, pp. 1054-1062, 1996. It was experimentally verified by R. Glynn Holt, Ronald A. Roy, "Measurements of bubble-enhanced heating from focused, mhz-frequency ultrasound in a tissue-mimicking material", Ultrasound in Medicine & Biology, Vol. 27, Issue 10, pp. 1399-1412, 2001.

The fact that the presence of the bubbles would have a positive influence on the thermal treatment is somewhat unexpected in view of earlier efforts to separate the cavitation and heating effects, since the microbubbles shadowed the region to be treated and might endanger the patient. (Bailey M R, Couret L N, Sapozhnikov O A, Khokhlova V A, ter Haar G, Vaezy S, Shi X, Martin R, and Crum L A, "Use of overpressure to assess the role of bubbles in focused ultrasound lesion shape in vitro," *Ultrasound Med Biol*, 27 (5), 695-708 (2001)). In U.S. Pat. No. 5,601,526, for example, is described how the presence of cavitation can lead to unwanted tissue destruction both inside of and outside of the focal zone, when applying focused acoustic power to achieve thermal effects. This patent teaches a method and apparatus for applying thermal and cavitation waves either separately or together so as to reduce the interaction between them. U.S. Pat. No. 5,573,497 teaches a method and apparatus for supplying the maximum thermal energy to a tissue while reducing or preventing cavitation.

Despite the efforts made in the past to separate the thermal from the cavitation effects of high intensity ultrasound on living tissue, the above cited reports attest to the difficulty and importance of harnessing the energy-concentrating effects of bubbles to do useful clinical work when exposed to ultrasound. The dominant heating mechanism depends on bubble size, medium shear viscosity and frequency-dependent acoustic attenuation. The bubble size distribution, in turn, depends on insonation control parameters (acoustic pressure, pulse duration), medium properties (notably dissolved gas concentration) and bubble shape irregularities that facilitate instabilities.

Ultrasound techniques have been applied therapeutically to such varied medical conditions as treatment of benign and malignant tumors of many types, varicose effects, destruction of gall and kidney stones, treatment of the esophagus, and unblocking blood vessels.

An illustrative example of a medical condition that can be treated by use of ultrasound is varicose veins and telangiectasia (spider veins). These veins are the visible surface manifestation of an underlying syndrome of venous insufficiency. The valves, which keep the blood moving towards the heart in normal veins, do not function properly and do not enable the blood to propagate, but to stagnate in the vein. The vein then dilates under the influence of increased venous pressure. Venous insufficiency syndromes allow venous blood to escape from its normal flow path and flow in a retrograde direction down into an already congested leg. Most patients with venous insufficiency have subjective symptoms that may include pain, soreness, burning, aching, throbbing, cramping, muscle fatigue, "restless legs" and unsightly appearance. Over time, chronic venous insufficiency leads to cutaneous and soft tissue breakdown that can be extremely debilitating.

Current treatments for varicose vein include: compression stockings, sclerotherapy (involves injection of chemical solution which causes scar tissue that closes the vein), endoluminal radiofrequency (RF) catheter and diode laser (uses RF or laser energy to coagulate the vein), phlebectomy (uses small incision to extract vein with phlebectomy hook), stripping (an operation performed under general anesthesia which involves the removal of the entire saphenous vein), and ligation (a surgical procedure that ties the saphenous vein and is optional when most of the valves are healthy). U.S. Pat. No. 6,436,061 teaches a method of applying focused ultrasonic energy to cause localized heating and damage the endothelial tissue of the vein such that the scarring of the healing tissue will at least partially block the flow of blood through the vein.

It is a purpose of the present invention to provide an apparatus and method for providing focused ultrasonic waves having a waveform at the focal point that can be modified to cause cavitation with no significant change in temperature, only increase of the temperature with minimal cavitation, suppression of cavitation, or a combination of these effects.

It is another purpose of the invention to provide ultrasound based therapies resulting from cavitation effects with no significant change in temperature, only increase of the temperature with minimal cavitation, suppression of cavitation, or a combination of these effects.

Further purposes and advantages of this invention will appear as the description proceeds.

SUMMARY OF THE INVENTION

In a first aspect the invention is a method of using ultrasound waves that are focused at a specific location in a medium to cause localized production of bubbles at that location and to control the production, and the cavitational and heating effects that take place there. According to the method of the invention, the production and control is accomplished by selecting the range of parameters of multiple transducers that are focused at the location in order to produce one of the waveforms chosen from the following group:
- a waveform comprising high negative peaks and small positive peaks, the waveform encouraging the creation of a cloud of microbubbles;
- a waveform encouraging the production of heat and the limitation the growth and possible implosion of said microbubbles; and
- a combined waveform comprising a spatial and/or temporal combination of two waveforms, one waveform comprising high negative peaks and small positive peaks and the second waveform comprising high positive peaks and only small negative peaks, the combined waveform allowing control of the size distribution of the microbubbles and temporal changes of this distribution.

The waveform encouraging the production of heat can have many shapes including: a waveform comprising high positive peaks and only small negative peaks and a sinusoidal waveform. The waveform comprising high positive peaks and only small negative peaks can encourage the reduction of the size of the microbubbles.

In a preferred embodiment, the number of transducers used to carry out the method of the invention is three. The radius of the microbubbles is typically in the range from a fraction of a micron up to 100 or more microns, preferably the radius is between approximately 3 microns to 5 microns.

According to a preferred embodiment of the method of the invention, a control system measures the changes in tissue or the size of the bubbles and accordingly adjusts the waveform to include more negative peaks, more positive peaks, or more equal sized waves. The method of the invention can employ a temperature control system to modify the output of the transducers according to the measured temperature. Additionally, an ultrasound imaging or non-imaging system can be used to view and monitor the region being targeted, to monitor the generation of the microbubbles at the desired location, and control the system for one or more of the following purposes:
- so that the number of microbubbles will be as planned;
- for aiming the focused beam to the targeted location; and
- to re-align the beam to a different location.

The response at the half harmonic or at higher harmonics of the transmitted frequencies is used by the ultrasound imaging or non-imaging system to measure one or more of the following:

- the effect of the heating;
- the duration of the effect;
- the number of microbubbles generated within the targeted region; and
- the spatial distribution of the microbubbles generated within the targeted region.

According to a preferred embodiment of the method of the invention, multiple transducers are arranged in an array, designed so that their mechanical focus and their own focus combine at the same point in space. Preferably, the point in space can be moved by either shifting the whole array, by repositioning of individual transducers, or by phase shift of the excitation pulse. In the preferred embodiments, the ultrasonic waves transmitted by the different transducers are designed to produce by interference specific waveforms at the focal point, which are not produced at other locations. Preferably the region within the focal zone of all the transducers in which the specific waveform develops at significant intensities, is typically very small. In preferred embodiments the amplitudes of the waveforms are less than −3 DB of the maximum amplitude, at distances that are typically less than 1 mm away from the point of the maximum amplitude in the lateral directions and less than 1.5 mm away in the axial directions. The specific waveforms can be modified to produce one of the following effects:

- cause cavitation with no significant change in temperature;
- increase the temperature with minimal cavitation;
- suppress cavitation; and
- a combination of these effects.

The method of the invention can be used for therapeutic purposes. In these cases, the array is typically placed extracorporally, in close proximity to the organ to be treated, with ultrasound gel or water surrounding the ultrasound transducers and the space between it and the organ. The therapy can be chosen from the following group:

- occlusion of varicose veins and telangiectasia;
- activation of cellular (e.g. endothelial cell) processes in the body, by either localized pressure forces or shear forces that produce therapeutic responses or damage;
- therapy of cancerous tissue by cavitation damage and/or rapid hyperthermia, resulting in apoptosis, tissue ablation or necrosis;
- therapy of cancerous tissue by damage and closure of the supply and drainage vasculature by cavitation, and/or rapid hyperthermia via coagulation of the arteries supplying the tumor;
- ablation of ectopic foci or re-entry loops within the cardiac walls, mainly within the ventricular walls;
- thrombolysis of clotted or semi-clotted arteries, e.g. coronary arteries, the carotid arteries, cerebral arteries, peripheral arteries etc.
- lipolysis or other methods of disintegration of fat cells, either by the mechanism of microbubbles collapse and/or by hyperthermia, resulting in apoptosis and drainage of fat deposits;
- coagulation of internal bleedings within the body; and
- non-invasive surgery of internal tissues and organs, by disintegration of cells along the cut.

The method of the invention can be used for occlusing varicose veins and telangiectasia by following the steps of:

a) providing multiple transducers;
b) focusing the multiple transducers at the same location within the vein;
c) selecting the range of parameters of the multiple transducers to produce a waveform comprising high negative peaks and small positive peaks, the waveform encouraging the creation of a cloud of microbubbles;
d) continuing the production of the waveform until the cavitation causes destruction of cells and the initiation of scaring of the tissue at the location;
e) focusing the transducers at another location within the vein;
f) repeating steps (c), (d), and (e) until enough scaring has been initiated to cause occlusion of the vein;

if necessary, two additional steps are added between steps (d) and (e):

g) changing the range of parameters of the multiple transducers to produce a heating waveform, the waveform encouraging the production of heat at the location; and
h) continuing the production of the waveform until the heating causes destruction of cells and the initiation of scaring of the tissue at the location.

The method of the invention can be used for activation of cellular processes in the body to produce therapeutic responses or damage selected from the following group: localized drug delivery, gene therapy, and angiogenesis.

The method of the invention can be used for thrombolysis of clotted or semi-clotted arteries in coronary arteries, the carotid arteries, cerebral arteries, and peripheral arteries.

In another aspect, the invention is a system for producing ultrasound waves and focusing them at a specific location in a medium to cause localized production of bubbles at that location. The system of the invention can control the production of the waves and the cavitational and heating effects that take place. The system of the invention comprises:

- three or more arbitrary waveform signal generators;
- three or more wide-band power amplifiers;
- three or more transducers; and
- one workstation.

In preferred embodiments of the system of the invention the three or more transducers are arranged as an array, designed so that their mechanical focus and their own focus combine at the same point in space. Preferably, the point in space can be moved by either shifting the whole array, by repositioning of individual transducers, or by phase shift of the excitation pulse. The ultrasonic waves transmitted by the three or more transducers of the system of the invention are designed to produce by interference specific waveforms at the focal point, which are not produced at other locations. The region within the focal zone of all the transducers in which the specific waveform develops at significant intensities and the amplitudes of the waveforms are less than −3 DB of the maximum amplitude, are typically at distances less than 25 mm and preferably less than 1 mm away from the point of said maximum amplitude in the lateral directions and less than 10 mm and preferably less than 1.5 mm away in the axial directions. In preferred embodiments of the system of the invention, the specific waveforms can be modified to produce one of the following effects:

- cause cavitation with no significant change in temperature;
- increase the temperature with minimal cavitation;
- suppress cavitation; and
- a combination of these effects.

The system of the invention may further comprising an ultrasound imaging or non-imaging system and a control box. Preferably the ultrasound imaging or non-imaging system is controlled by the workstation to which it is connected through the control box and can be used to view and monitor the region being targeted, to monitor the generation of the microbubbles at the desired location, and control the system for one or more of the following purposes:
- so that the number of microbubbles will be as planned;
- for aiming the focused beam to the targeted location; and
- to re-align the beam to a different location.

In preferred embodiments of the system of the invention the response at the half harmonic or at higher harmonics of the transmitted frequencies is used by the ultrasound imaging or non-imaging system to measure one or more of the following:
- the effect of the heating;
- the duration of the effect;
- the number of microbubbles generated within the targeted region; and
- the spatial distribution of the microbubbles generated within the targeted region.

In a preferred embodiment of the invention, the ultrasound imaging or non-imaging system measures the changes in tissue or the bubbles size and the control box and workstation accordingly adjust the waveform to include more negative peaks, positive peaks, or equal sized waves.

The system of the invention may further comprise a temperature measurement system. The temperature measurement system may comprise one or more thermocouples and is preferably used to modify the output of the transducers according to the measured temperature.

The system of the invention may be adapted for use in therapeutic procedures; wherein the array is placed extra-corporally, in close proximity to the organ to be treated, with ultrasound gel or water surrounding the ultrasound transducers and the space between it and the organ. The system of the invention may be adapted for use in any of the therapeutic procedures in the following group:
- occlusion of varicose veins and telangiectasia;
- activation of cellular (e.g. endothelial cell) processes in the body, by either localized pressure forces or shear forces that produce therapeutic responses or damage;
- therapy of cancerous tissue by cavitation damage and/or rapid hyperthermia, resulting in apoptosis, tissue ablation or necrosis;
- therapy of cancerous tissue by damage and closure of the supply and drainage vasculature by cavitation, and/or rapid hyperthermia via coagulation of the arteries supplying the tumor;
- ablation of ectopic foci or re-entry loops within the cardiac walls, mainly within the ventricular walls;
- thrombolysis of clotted or semi-clotted arteries, e.g. coronary arteries, the carotid arteries, cerebral arteries, peripheral arteries etc.
- lipolysis or other methods of disintegration of fat cells, either by the mechanism of microbubbles collapse and/or by hyperthermia, resulting in apoptosis and drainage of fat deposits;
- coagulation of internal bleedings within the body; and
- non-invasive surgery of internal tissues and organs, by disintegration of cells along the cut.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The invention relates to a system for creating ultrasound waves and causing them to travel through a liquid and to methods for controlling the waveform of the ultrasound to cause localized production of bubbles in the liquid and for control of the resultant cavitational and heating effects. The invention is particularly suited to the use of ultrasound for the localized production of bubbles for therapeutic purposes. The therapy is based on cavitation effects accompanied by minimal heating and/or by bubble induced heating of the location at which the bubbles are produced.

The invention is based on the recognition that the creation and growth rates of the bubbles formed in a fluid by ultrasonic waves traveling through it is dependent to a large extent on the waveform of the waves. Instead of the sinusoidal waveform that is normally used to cause rectified diffusion, the invention selects the range of parameters including frequency, phase, and amplitudes of multiple transducers to produce two basic waveforms in the region of interest. The first waveform comprises high negative peaks and small positive peaks, which encourages the creation of a cloud of microbubbles. The second waveform is a waveform which produces heat, such a waveform can have several forms e.g. a sinusoidal wave form or a waveform that comprises high positive peaks and only small negative peaks. The second waveform preferably includes the range of control parameters that assures that the ultrasound energy is more absorbed than scattered by the microbubbles by keeping them small (e.g. smaller than approximately 3-5 microns in radius).

To produce the waveforms of the invention, at least three independent high-power focused ultrasound transducers are used, housed within a structure that produces a common focus. Each transducer is powered by its own amplifier, which is driven by a signal generator, usually tuned to a different frequency. An optional part of the invention is that the method and system may also include a control system that measures the changes in tissue or the size of the bubbles and accordingly adjusts the waveform to include more negative peaks, positive peaks or equal sized waves.

Figure 2:
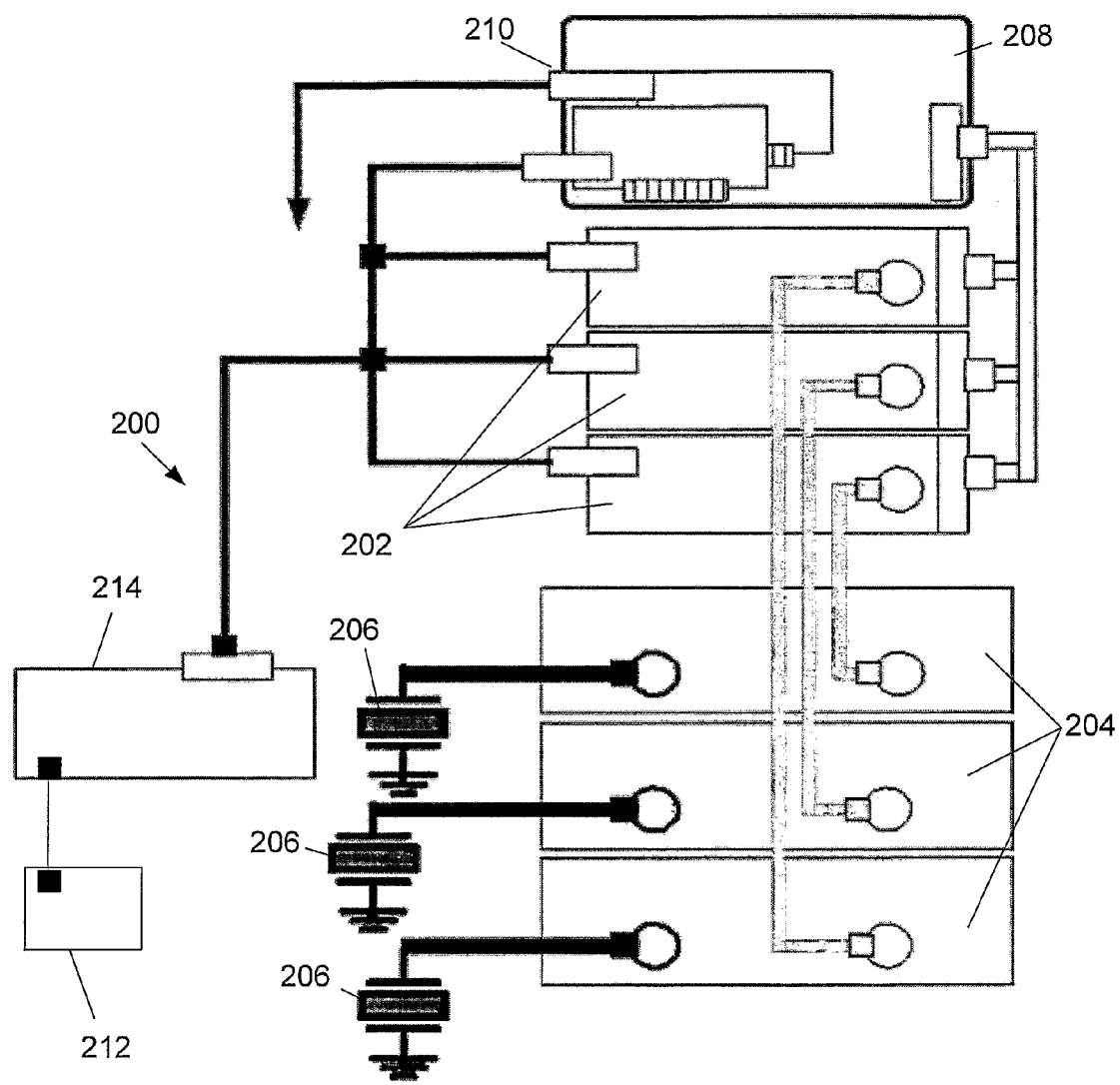
FIG. 2 schematically shows the control and driving system for carrying out the invention.

One embodiment of the control and driving system for carrying out the invention is shown schematically in FIG. 2. In this embodiment, the control and driving system 200 includes three arbitrary waveform signal generators 202 connected to three wide-band power amplifiers 204 and through impedance matching to the three transducers 206. At least one workstation 208, for example a personal computer (PC), controls the timing of activation and amplitude of each arbitrary waveform signal generator 202 by means of different protocols and separate cables for each signal generator. The workstation 208 may also control a temperature measurement system 210 that measures and records temperatures, for example with thermocouples and may modify the therapy according to the measured temperatures. Additionally or alternatively, an ultrasound imaging or non-imaging system 212 may be used to view and monitor the region being treated (targeted) to monitor the generation of the microbubbles at the desired location and control the system so that the number of microbubbles will be as planned and/or may be used for aiming the focused beam to the targeted region and/or to re-align the beam to a different location. The cavitation effects can be detected by many different techniques that are known to skilled persons. For example: use of a single transducer operating at ½, ⅓, ¼, etc. of the frequency of one of the transducers in the array as a detector; use of a single transducer operating at 1.5, 2.5, 3.5, etc. harmonic; use of a "white noise" detector; use of a pair of transducers working continuously as a transmitter-receiver pair; or use of a single transducer, that both transmits and receives the reflected signal. The ultrasound imaging system 212 may be used additionally or alternatively to monitor the treatment during the increased temperatures regime by measuring the effect of the heating, the duration of the effect, the number and the spatial distribution of the microbubbles generated within the treated region by using the response at the second harmonic or half harmonic of the transmitted frequencies. The ultrasound system monitoring system 212 may be controlled by the workstation 208 to which it is connected through control box 214.

Control and driving system 200 is comprised of standard components that are well known to persons familiar with the use of ultrasound for diagnostic or therapeutic purposes. Typical but non-limitative examples of commercially available components that are suitable for use in Control and driving system 200 are: arbitrary waveform signal generator 202—Tabor Electronics Ltd., model 8025; wide-band 10 kHz-100 MHz power amplifier 204—Acoustic Research, model 150A100B; transducer 206—Imasonic, model no. T3035A101, T3034A101, T2336A101; workstation 208—HP-Compaq PC; temperature measurement system 210—Omega thermocouples, model no. TGC150-CPSS-150-SMP-MUK270502, National Instruments Temperature measurement board model no. NI-4351, Temperature I/O box model no. TC-2190, and National Labview software; ultrasound imaging system 212—GE Healthcare model VIVID III; and control box 214—HP-Compaq PC running National Instruments Labview software, National Instruments I/O box, model no. BNC-2090, and National Instruments DAQ board model no. PC-LPM-16.

The power transducers 206 are arranged as an array, designed so that their mechanical focus and their own focus combine at the same point in space. This point in space can be moved by either shifting the whole array, by repositioning of individual transducers, or by phase shift of the excitation pulse. The ultrasonic waves transmitted by the different transducers are designed to produce by interference specific waveforms at the focal point, which are not produced at other locations. These specific waveforms can be modified to cause cavitation with no significant change in temperature, increase of temperature with minimal cavitation, suppression of cavitation, or a combination of these effects. The region in which the specific waveforms develop at significant intensities, i.e. within the focal zone of all transducers, is usually very small, where the amplitudes of −3 DB and less of the maximum, are typically less than 1 mm away from the point of maximum in the lateral directions and, less than 1.5 mm away in the axial directions.

Figure 3A:
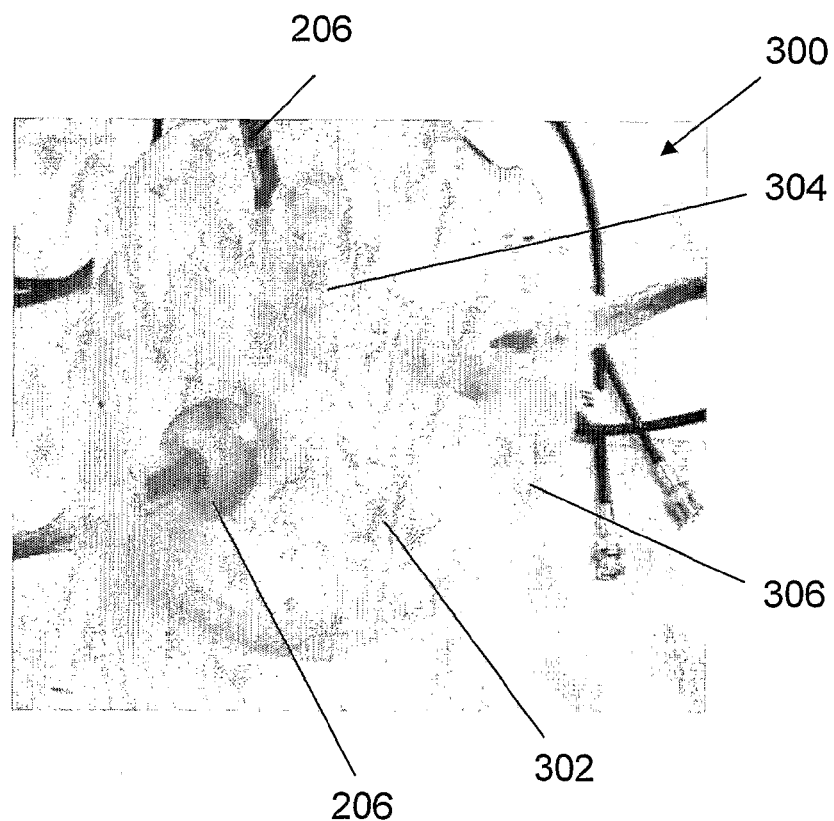
FIG. 3A and FIG. 3B show an embodiment of an array of transducers that is suitable for use in the invention.
Figure 3B:
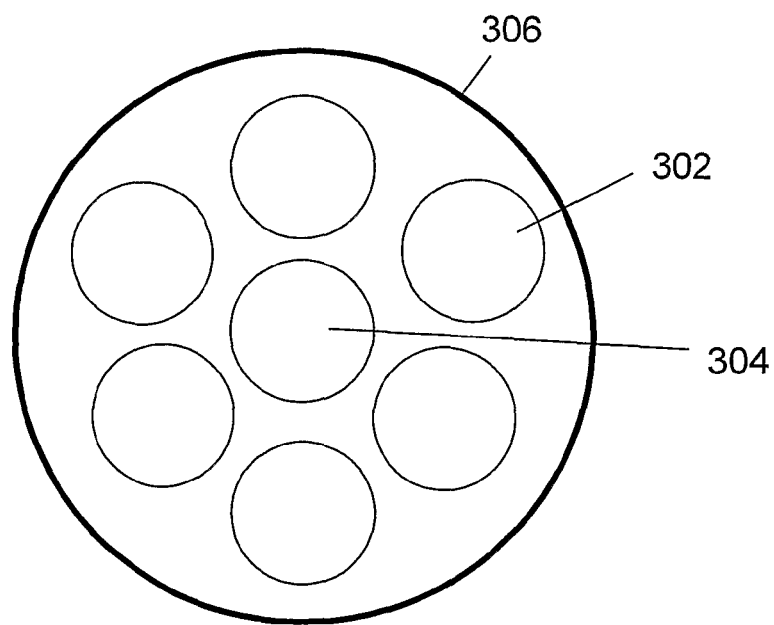

An embodiment of an array of transducers 300 that uses cylindrical power transducers suitable for use in the invention is shown in FIG. 3A and FIG. 3B. Another embodiment, using annular transducers is described with reference to FIG. 15A to 15D hereinbelow. FIG. 3A is a photograph showing the array 300 from the top. Array 300 is mounted in a cylindrically shaped holder 306 made of plexiglass or other suitable material. In the embodiment shown, holder 306 comprises a central bore 304 coaxial with the symmetry axis of holder 306 and six other bores 302 arranged symmetrically around bore 304 and inclined at an angle with the symmetry axis. Array of transducers 300 can thereby comprise up to six cylindrical power transducers 206 which are inserted into bores 302 such that all are physically aimed at the same focal point. The focal point of the array of ultrasound transducers 300 depends, upon other factors on the medium through which the ultrasound waves will be transmitted. A typical focal distance in water for array 300 is six cm from the bottom face of transducer holder 306. This focal distance is equivalent to five cm in gel and four cm in liver tissue. The center bore 304 can be used for an imaging probe connected to an imaging system 212 or for inserting thermocouples that are components of temperature measurement system 210. FIG. 3B schematically shows the arrangement of the bores 302 and 304 on the planar bottom face of holder 306.

The holder 306 is designed such that array 300 can be placed extra-corporally, in close proximity to the organ to be treated, with ultrasound gel or water surrounding the ultrasound transducers and the space between it and the organ.

Figure 4:
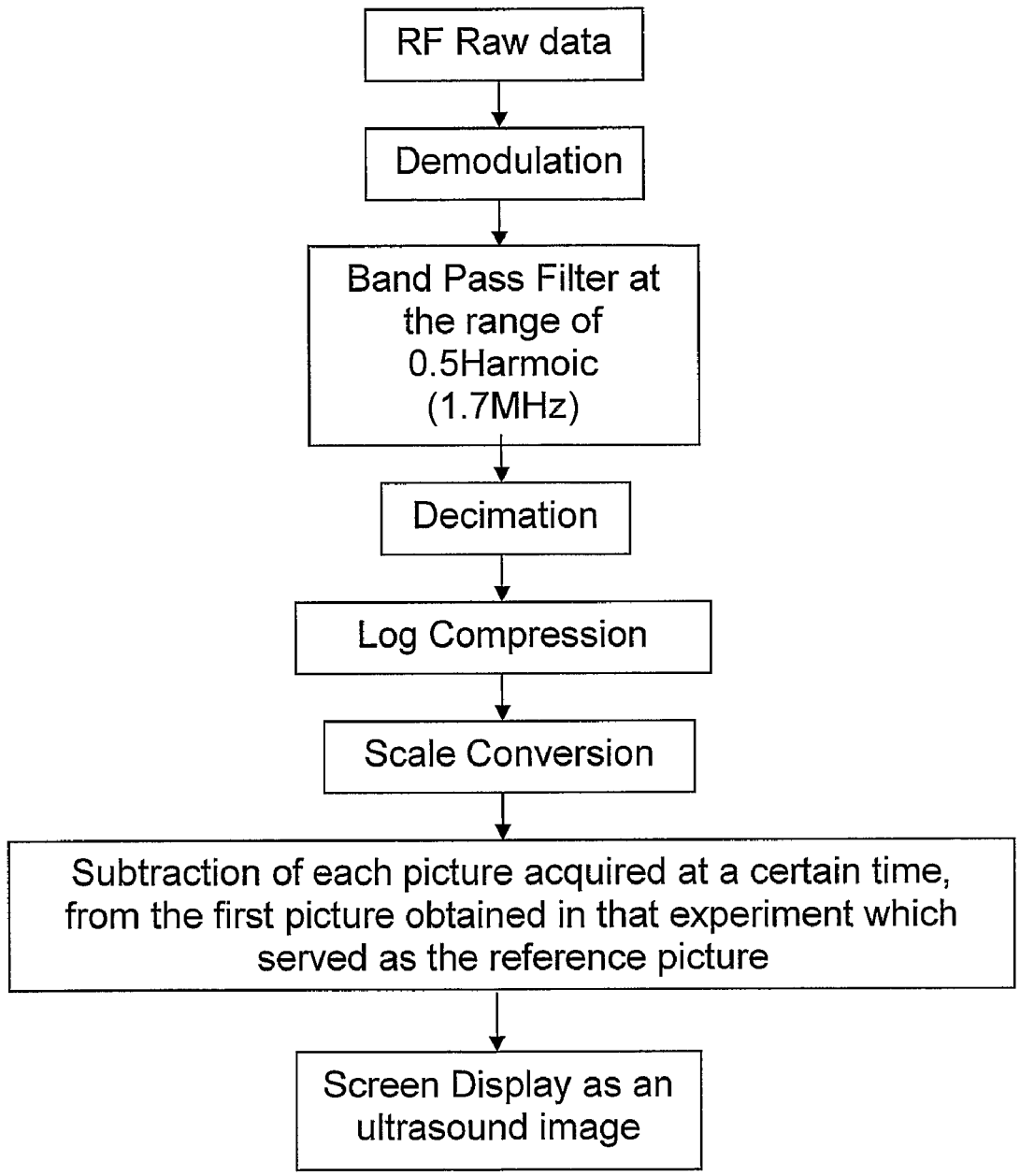
FIG. 4 is a flow-chart showing the sequence of operations in an example of a typical data processing scheme used to measure and display the existence, number, size, location and spatial distribution of microbubbles generated during implementation of the method of the invention.

As mentioned hereinabove, ultrasound system 200 may be either imaging or non-imaging and in the preferred embodiment of the invention is used to measure the number of microbubbles, their location in space, and their spatial population distribution. These measurements can be made during any phase of the process, for example when bubbles are generated during the cavitation phase, during a heating phase, or a phase when it is desired to reduce or enlarge the size and/or number of microbubbles. FIG. 4 is a flow-chart showing the sequence of operations in an example of a typical data processing scheme used to measure and display the existence, number, size, location and spatial distribution of microbubbles generated during implementation of the method of the invention. The steps listed in the flow chart of FIG. 4 are conventional ones for processing ultrasound signals, which are mainly executed automatically using equipment and software familiar to skilled persons who will require no further explanation of the data processing scheme. The measurements made using the scheme outlined in FIG. 4, or any equivalent scheme known to skilled persons, may be used to modify the operation of the system so as to increase, reduce, or shift the number of microbubbles, or their sizes. The modification can be made either manually or automatically using software provided with the workstation 208, ultrasound system monitoring system 212, and/or control box 214.

The goals of the invention are achieved by selecting the range of parameters, including frequency, phase, and amplitude, of each one of the multiple transducers to produce the desired waveform in the region of interest. Using the method of the invention, bubbles having a size ranging from a fraction of a micron up to 100 or more microns with the presently preferred range for the therapies discussed hereinbelow being between approximately 3 and 5 microns. Similarly the size of the focal area can be varied between spots that are typically less than 25 mm radius, and preferably less than 1 mm, radius in the lateral directions and less than 10 mm, and preferably less than 1.5 mm, long in the axial directions. The ability to achieve such a small focal zone length in the axial direction by using the method and apparatus of the invention provides a significant improvement in the ability to provide localized treatment for various conditions over the prior art methods in which the focal zone length typically ranges between 10 mm and 20 mm. The minimum size of the treatment area is on the order of the minimum size of the focal area and, by means of electrically or mechanically scanning the combined beams and/or the array of transducers, the maximum size of the treatment area is unlimited.

Figure 5:
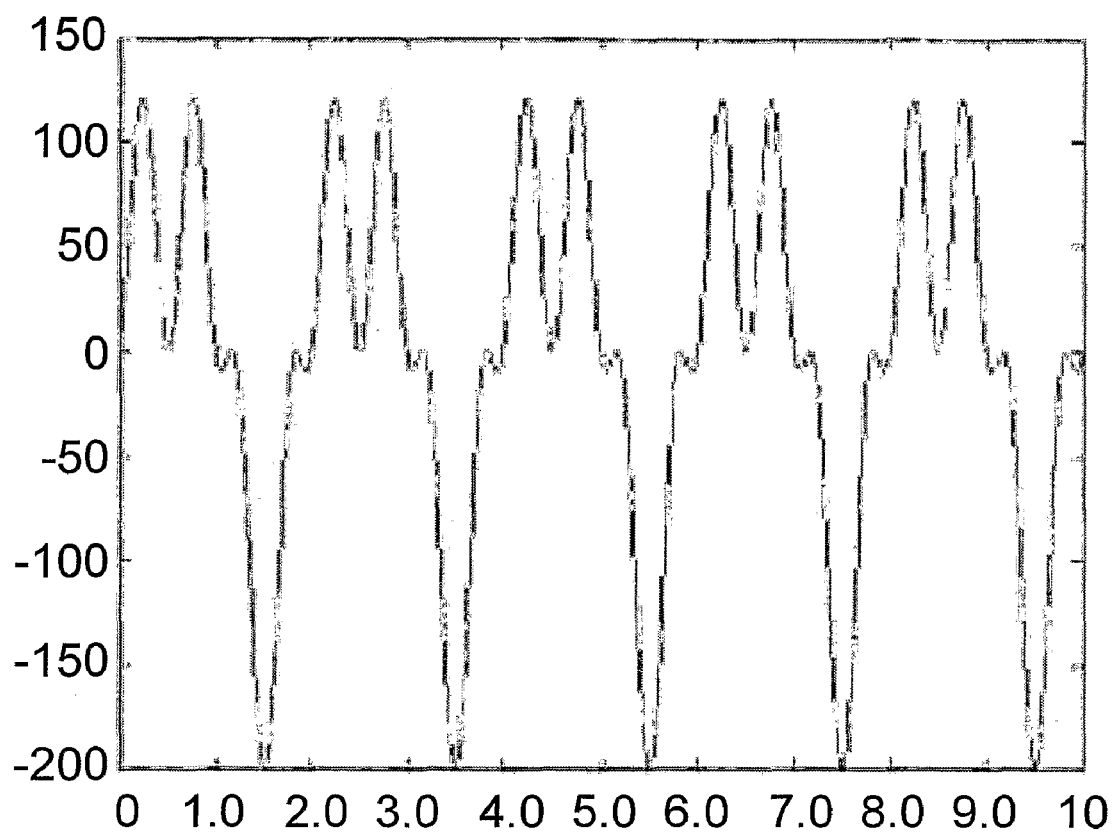
FIG. 5 shows a waveform comprising high amplitude negative peaks and small amplitude positive peaks.

FIG. 5 shows a waveform comprising high negative peaks and small positive peaks. This type of waveform, by increasing the ratio of the amplitudes of the de-compression part of the acoustic wave to the compression part, encourages the creation of a cloud of microbubbles. In FIG. 5, the horizontal axis represents time measured in μsec and the vertical axis the amplitude of the signal at the focus measured in volts. The signal shown in FIG. 5 was generated, using the system shown in FIG. 2 and the array shown in FIG. 3A comprising three transducers, by a hydrophone that converts accurately the acoustic pressure at that point to volts. The control and driving system operated at the frequencies, phases, and amplitudes shown in Table 1 in order to produce the waveform shown in FIG. 5.

TABLE 1

| Transmission frequency | Output Voltage of Signal Generator | Output Voltage of Power Amplifier | Gain setting of Power Amplifier | Phase of the signal |
|---|---|---|---|---|
| 0.5 MHz | 180 mV | 165 V | 90% | 0° |
| 1.0 MHz | 100 mV | 80 V | 90% | 90° |
| 2.0 MHz | 100 mV | 37 V | 100% | 270° |

Figure 6:
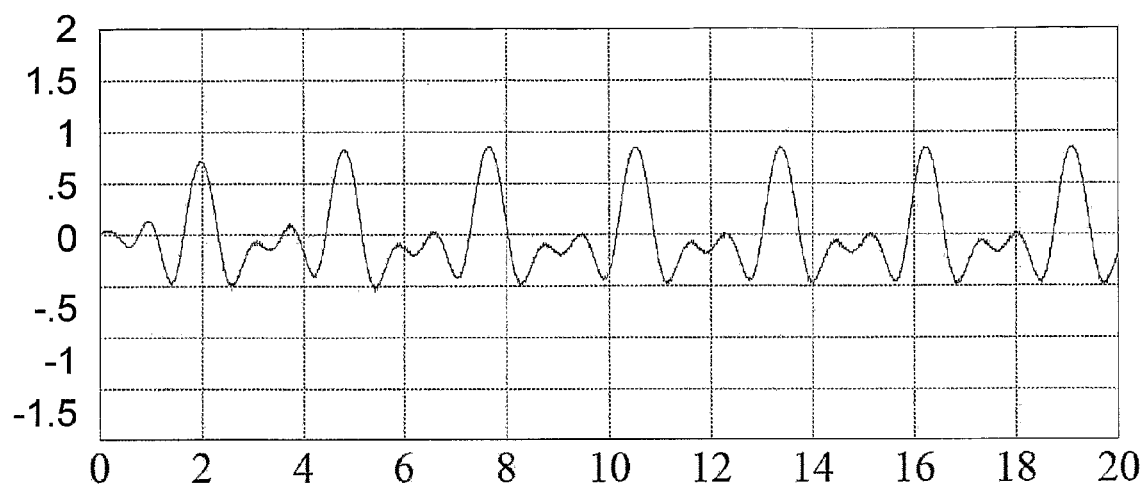
FIG. 6 shows a waveform comprising high amplitude positive peaks and only small amplitude negative peaks.

FIG. 6 shows a waveform comprising positive peaks and only small negative peaks. This type of waveform, by decreasing the ratio of amplitudes of the de-compression part of the acoustic wave to the compression part, tends to keep the microbubbles small thereby assuring that the ultrasound energy is more absorbed than scattered and producing heat. In FIG. 6, the horizontal axis represents time measured in μsec and the vertical axis the amplitude of the signal at the focus measured in volts. The signal shown in FIG. 6 was generated, using the system shown in FIG. 2 and the array shown in FIG. 3A comprising three transducers, by a hydrophone that converts accurately the acoustic pressure at that point to volts. The control and driving system operated at the frequencies, phases, and amplitudes shown in Table 2 in order to produce the waveform shown in FIG. 6.

TABLE 2

| Transmission frequency | Output Voltage of Signal Generator | Output Voltage of Power Amplifier | Gain setting of Power Amplifier | Phase of the signal |
|---|---|---|---|---|
| 0.5 MHz | 350 mv | 290 v | 90% | 0° |
| 1 MHz | 200 mv | 160 v | 90% | 90° |
| 2 MHz | 300 mv | 70 v | 100% | 270° |

FIG. 7 to FIG. 11 are graphs showing the results of a series of experiments that were carried out to measure the effect of applying cavitation and heating waveforms at different power levels and the effect of the duration of applying the heating waveform on the temperature. The experiments were carried out in an artificial gel phantom, which was prepared using a beaker filled with 0.8 L of ethylene Glycol in distilled water at a ratio of 1.3:1 by volume, and heated to 70° C. 85 gm of gelatin powder was then added slowly while the solution was constantly stirred. When the solution was gelled it was centrifuged to exclude bubbles, and then 170 ml of formaldehyde were added. The mixture was poured into a glass container. This gel does not liquidize even at 120° C. The experiments were carried out using the system described hereinabove to generate the ultrasound waveforms. For the sake of simplicity, during the heating stage only the amplitudes of the waveform generators were modified, and not their phase. This caused the acoustic pressure waveform to resemble a sine wave, similar to that shown in FIG. 1, and not the waveform depicted in FIG. 6. The parameters used during the heating period (in all of the experiments shown in FIG. 7 to FIG. 11) are shown in Table 3.

TABLE 3

| Transmission frequency | Output Voltage of Signal Generator | Output Voltage of Power Amplifier | Gain setting of Power Amplifier | Phase of the signal |
|---|---|---|---|---|
| 0.5 MHz | 350 mv | 290 v | 90% | 0° |
| 1 MHz | 200 mv | 160 v | 90% | 90° |
| 2 MHz | 300 mv | 0 v | 100% | 270° |

FIG. 7 through FIG. 11 show temperature in degrees centigrade (vertical axis) vs. time in seconds (horizontal axis) measured with thermocouples placed at the focal region for three different power levels used during the cavitation period. During the first stage, the cavitation period, the experiments were performed at three different power levels, the parameters of which are shown in Table 4. During the second stage, the heating period, the power level and parameters (as given in Table 3) were always kept the same.

TABLE 4

| Output Voltage of the Signal | Output Voltage of the Power | Output Voltage of the Signal Generator | Output Voltage of the Power Amplifier | Output Voltage of the Signal | Output Voltage of the Power | Gain setting of the | Phase |
|---|---|---|---|---|---|---|---|

| Transmission frequency | Generator Lowest power level | Amplifier Lowest power level | Intermediate power level | | Generator Highest power level | Amplifier Highest power level | Power Amplifier | of the signal |
|---|---|---|---|---|---|---|---|---|
| 0.5 MHz | 180 mV | 165 V | 360 mv | 330 v | 540 mv | 495 v | 90% | 0° |
| 1.0 MHz | 100 mV | 80 V | 200 mv | 160 v | 300 mv | 240 v | 90% | 90° |
| 2.0 MHz | 100 mV | 37 V | 200 mv | 74 v | 300 mv | 111 v | 100% | 270° |

Figure 7:
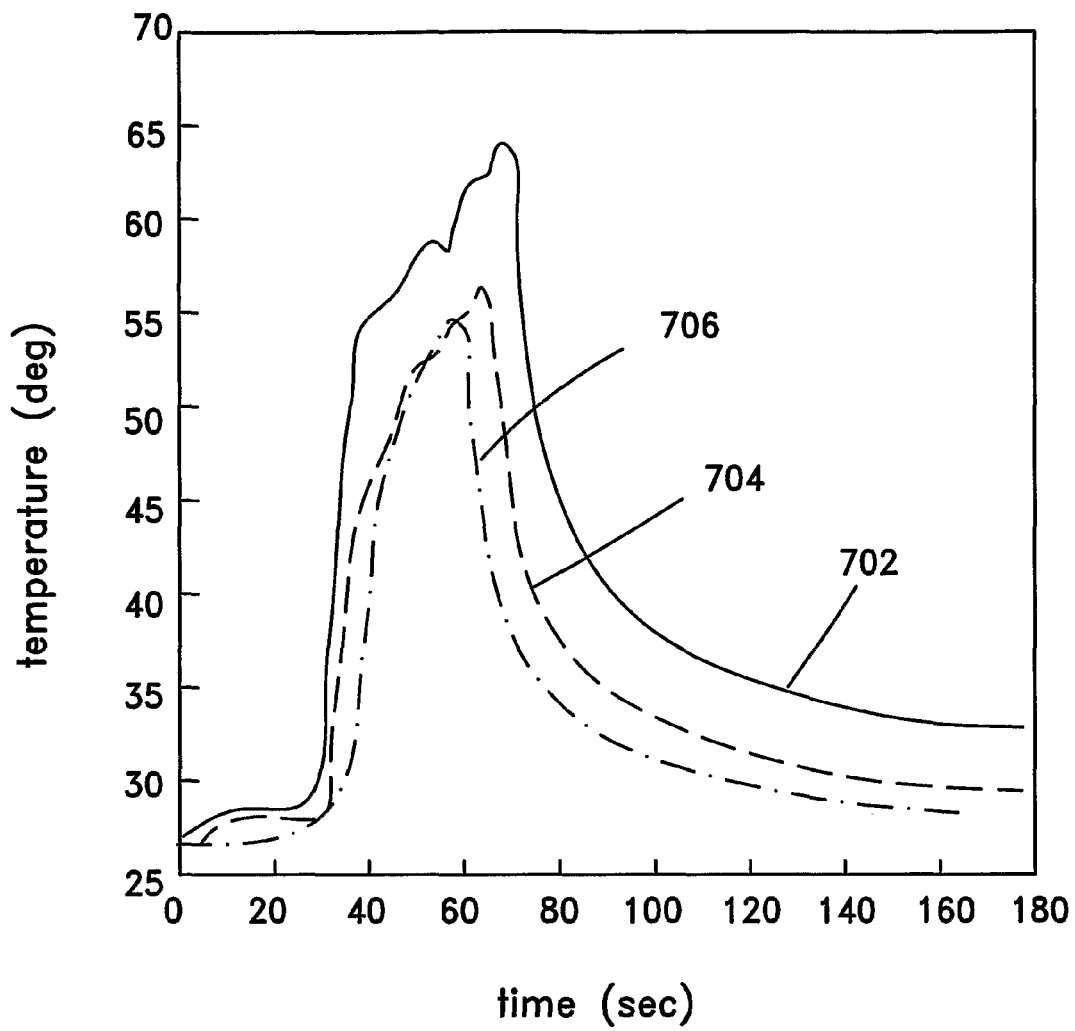
FIG. 7 to FIG. 11 are graphs showing the results of a series of experiments that were carried out to measure the effect of applying cavitation and heating waveforms at different power levels and the effect of the duration of applying the heating waveform on the temperature.
Figure 8:
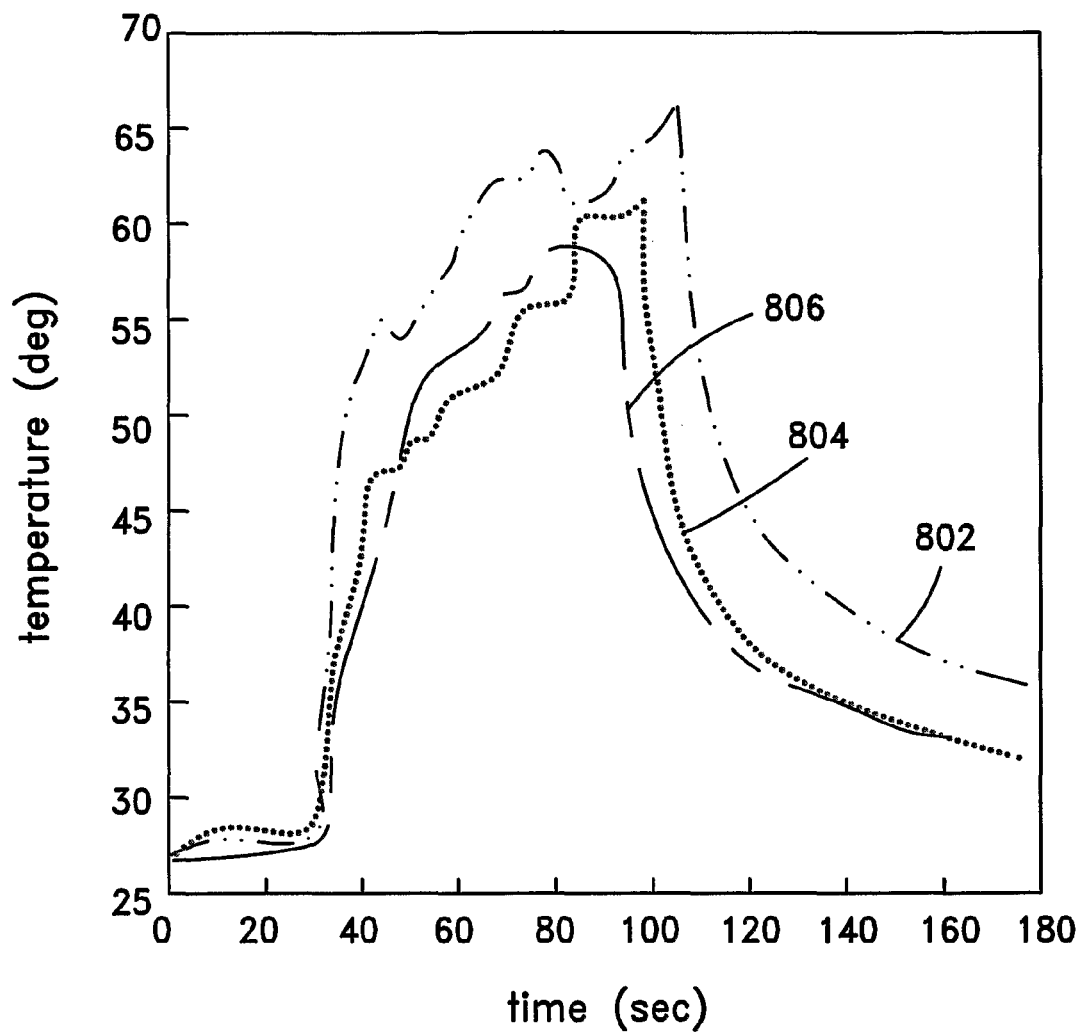

In FIG. 7 the waveform shown in FIG. 5 was generated for 30 sec followed by the heating waveform for an additional 30 sec. In FIG. 8 the waveform shown in FIG. 5 was generated for 30 sec followed by the heating waveform for an additional 60 sec. The lines shown in FIGS. 7 and 8 are the mean of 5 experiments. Lines 702 and 802 are the results at the highest power level, 704 and 804 at the intermediate power level, and 706 and 806 at the lowest power level used during the cavitation period. In all cases, essentially no heat was generated during the 30 sec cavitation period when the waveform of FIG. 5 was applied. During the period that the heating waveform was applied the temperature rose as expected with a sharp drop off in temperature as soon as the generation of the ultrasound signals ceased. The number of bubbles generated at the focus increases as the power level is increased during the cavitation phase. This effect is seen in the graphs, which show an increase of the maximum temperature caused by the increase power during the cavitation phase despite the fact that during the heating period the transmitted energy remains the same.

Figure 9:
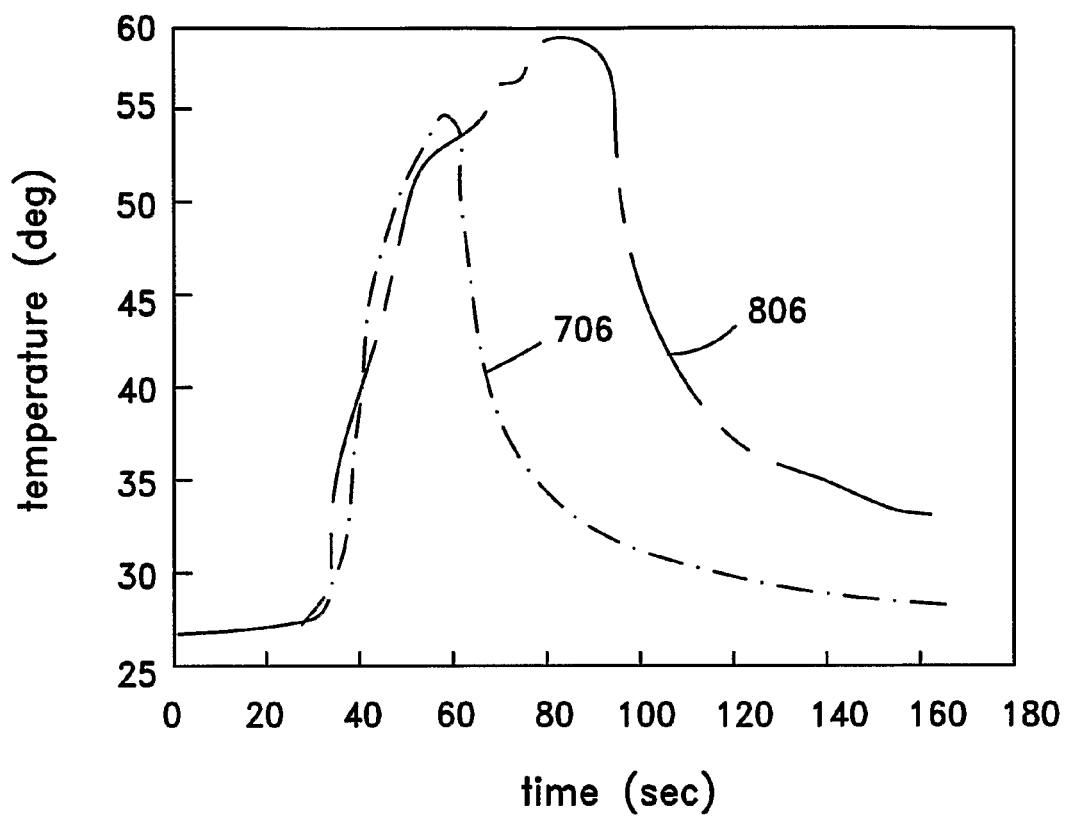
Figure 10:
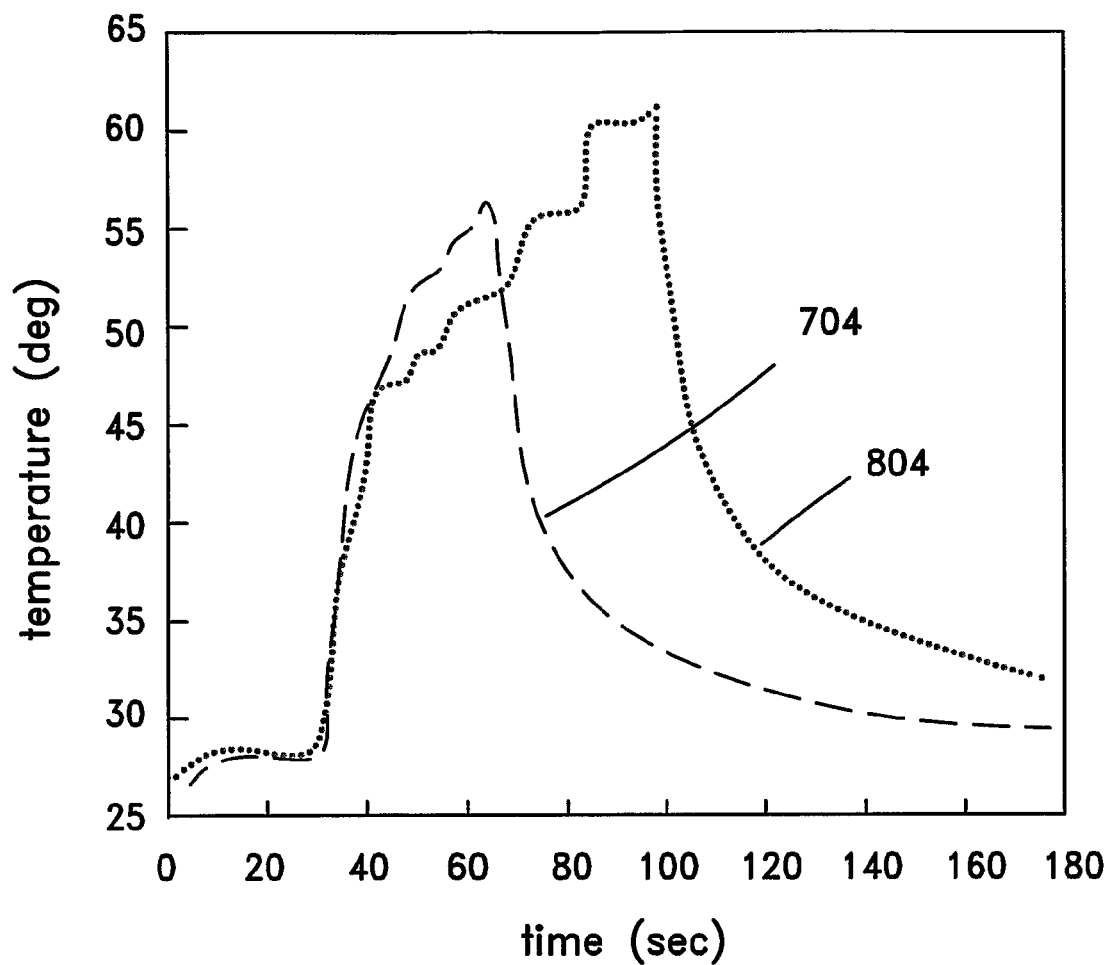
Figure 11:
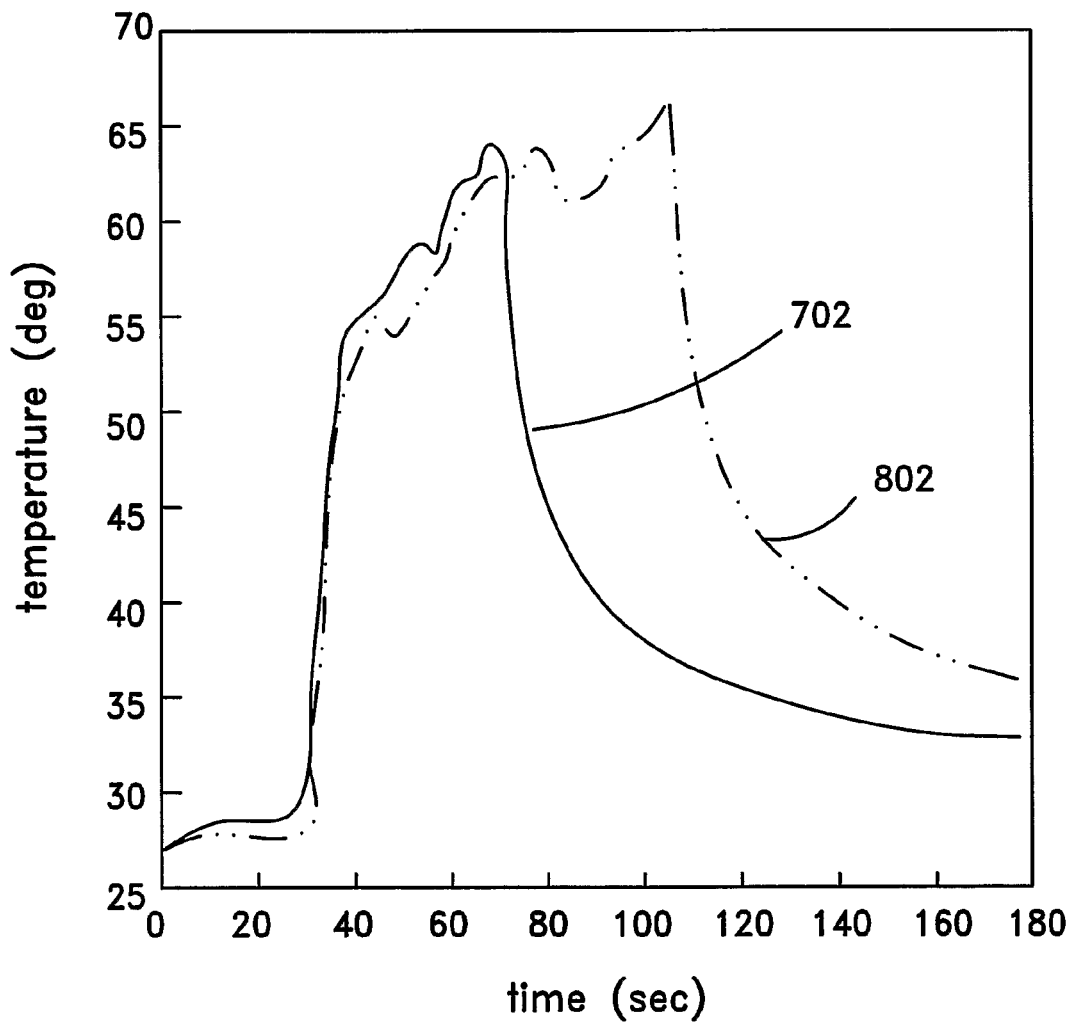

The effects of different durations of the heating period are displayed in FIGS. 9, 10, and 11 for the low, medium, and power levels respectively. From these graphs it can be seen that the longer duration of heating causes some additional rise of temperature.

Figure 1:
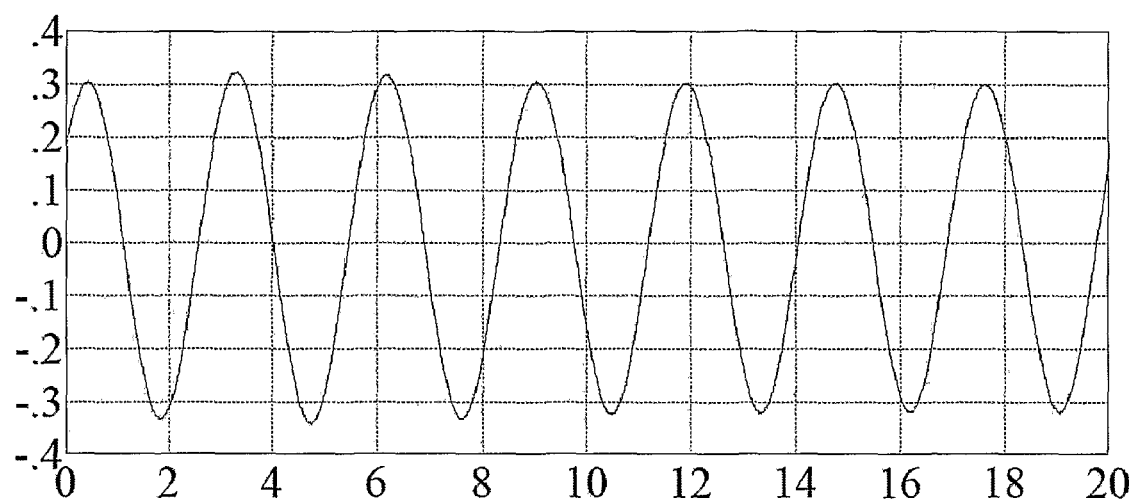
FIG. 1 shows an ultrasound signal having a sinusoidal waveform.

When the waveform of FIG. 5 was not generated in experiments similar to the above and the waveform of either FIG. 6 or FIG. 1 was focused in the medium for a period of 60 sec, the maximal mean temperature reached was 36.88 C°.

Images displayed on a screen of a representative example of the results of the sequence of operations that are outlined in the flow-chart in FIG. 4 are shown in FIGS. 12A to 12D. The images are produced by attainment of the raw data, as produced by the ultrasound transducer that acquires the echoes from the gel, and off-line processing by the control box 214 of the raw data as described by flow chart of FIG. 4. The results shown in these figures are of measurements made using the medium power level and the specially designed gel phantom described that does not melt at high temperatures. The gel was prepared with degassed water and spun in a centrifuge to reduce to a minimum the number of dissolved gases and the existence of microbubbles.

Figure 12A:
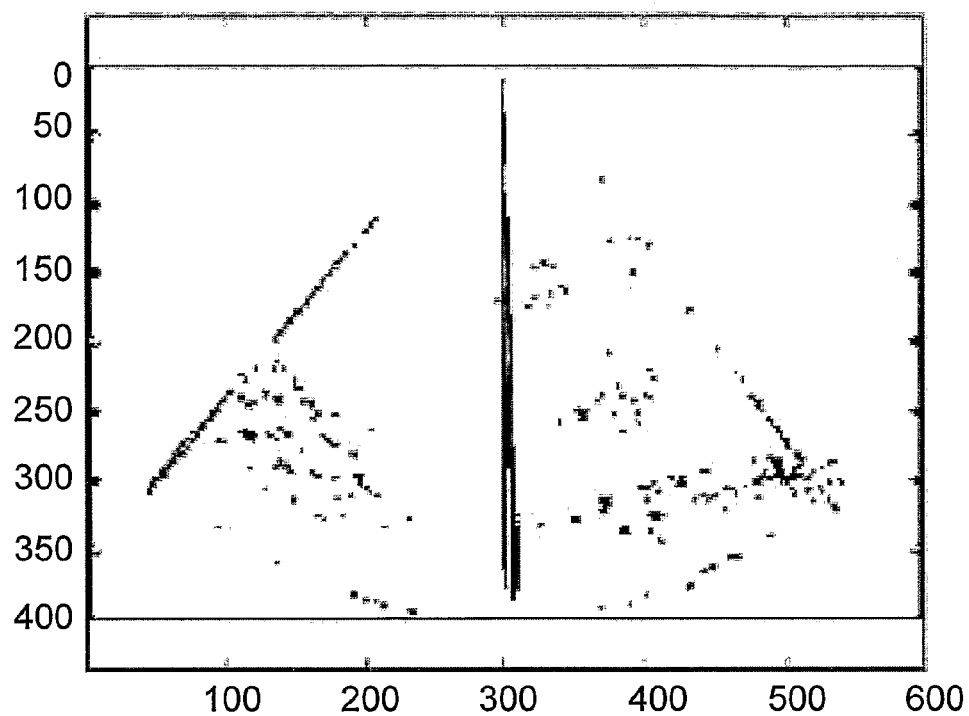
FIGS. 12A to 12D show the results of a representative example of the sequence of operations that are outlined in the flow-chart in FIG. 4 as displayed on a screen.
Figure 12B:
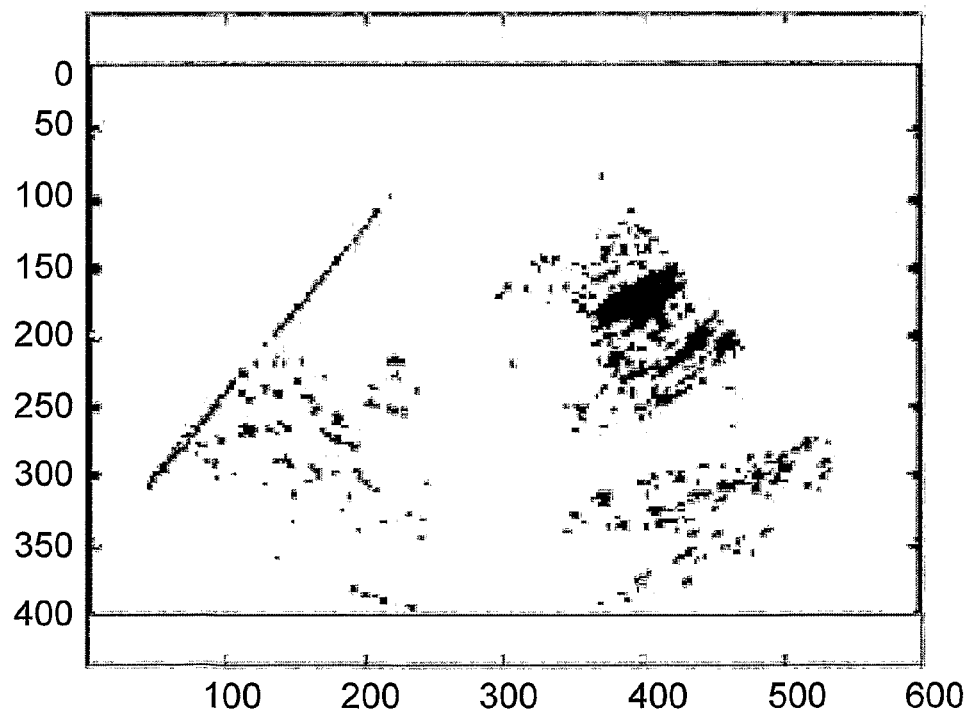
Figure 12C:
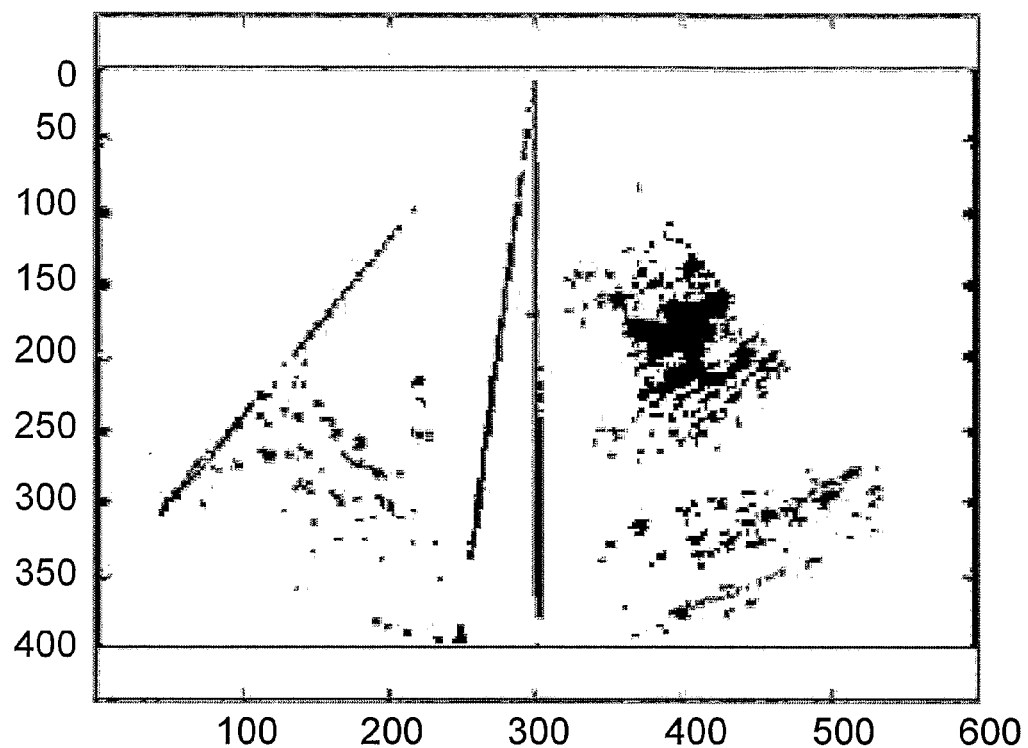
Figure 12D:
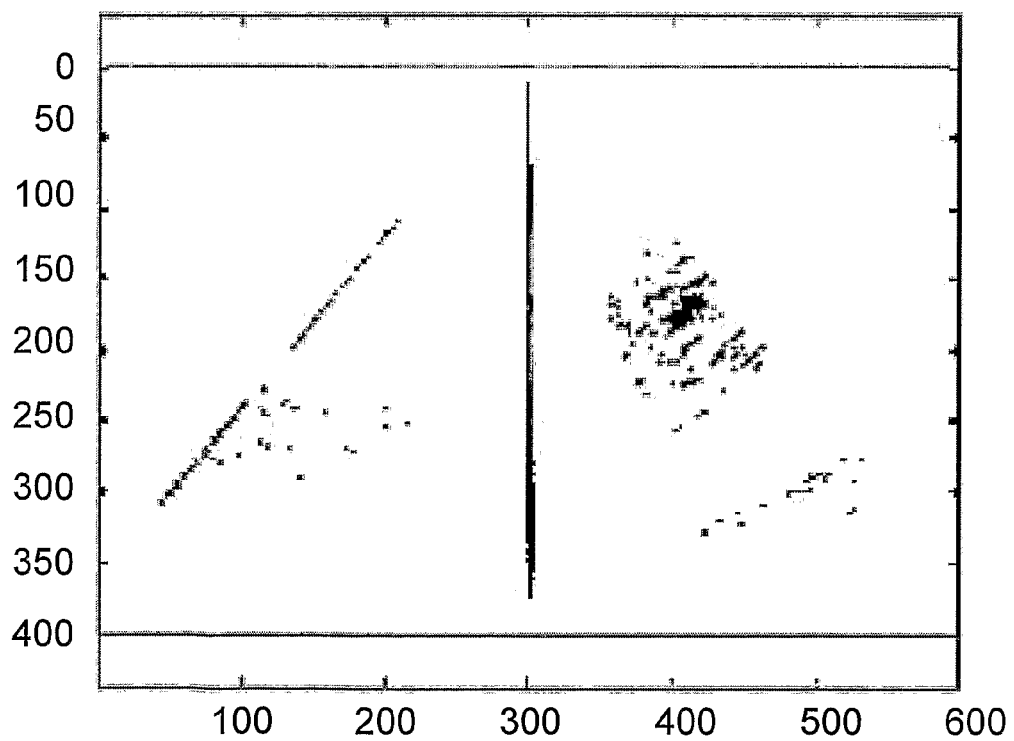

The image in FIG. 12A was acquired after 2 see of operation of the cavitation period (waveform of FIG. 5) and no bubbles are noticed (the straight lines are artifacts of the RF line acquisition). Microbubbles are formed after 16 see of operation of the cavitation period as can be seen in the image in FIG. 12B. FIG. 12C shows the result after 30 see of operation of the cavitation period. The number of bubbles has increased without translation towards the transducers, as is commonly observed. The image in FIG. 12D was acquired after an additional 30 see of heating when the number of microbubbles was reduced.

Figure 13:
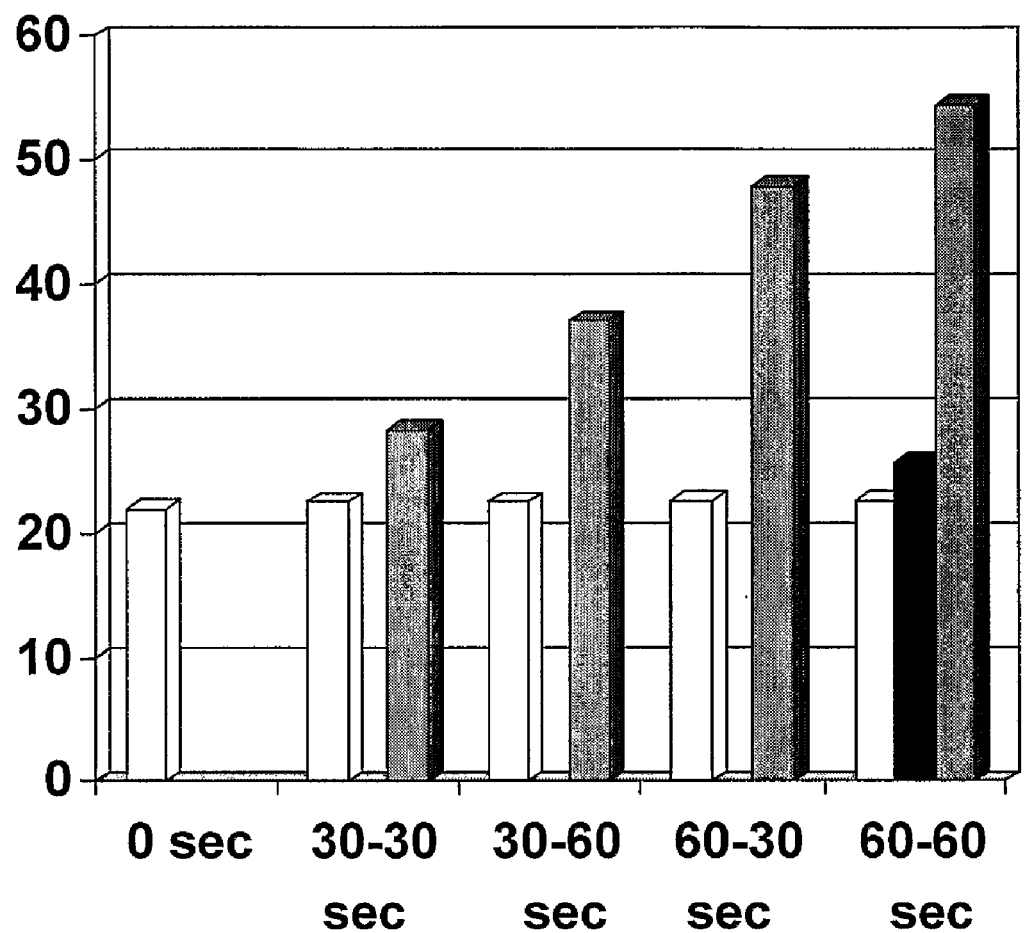
FIG. 13 is a bar chart depicting the temperature values after different durations of production of cavitation and heating in excised liver tissue.

The same experiment as above was repeated in vitro using fresh liver as the phantom. The liver was kept in saline solution at room temperature (22 C°), and the array of transducers was aimed at a specific point in the tissue. Several experiments were performed in which the system was operated for the following durations:

30 see cavitation followed by 30 sec heating
30 sec cavitation followed by 60 see heating
60 see cavitation followed by 30 sec heating
60 sec cavitation followed by 60 see heating
60 see cavitation only
60 sec heating only
60 sec of no cavitation followed by 60 sec of no heating The bar chart in FIG. 13 depicts the temperature values (° C.) on the vertical axis after the different durations of production of cavitation and heating listed above. In FIG. 13, the white bars represent cavitation only (waveform of FIG. 5), the black bar represents heating only (waveform of FIG. 6), and the gray bars cavitation followed by heating. The white bar on the left represents ambient temperature.

Investigation of the excised liver tissue after the production of cavitation followed by heating clearly showed a small area that went through denaturation in a cut in the middle of the treated region.

Figure 14:
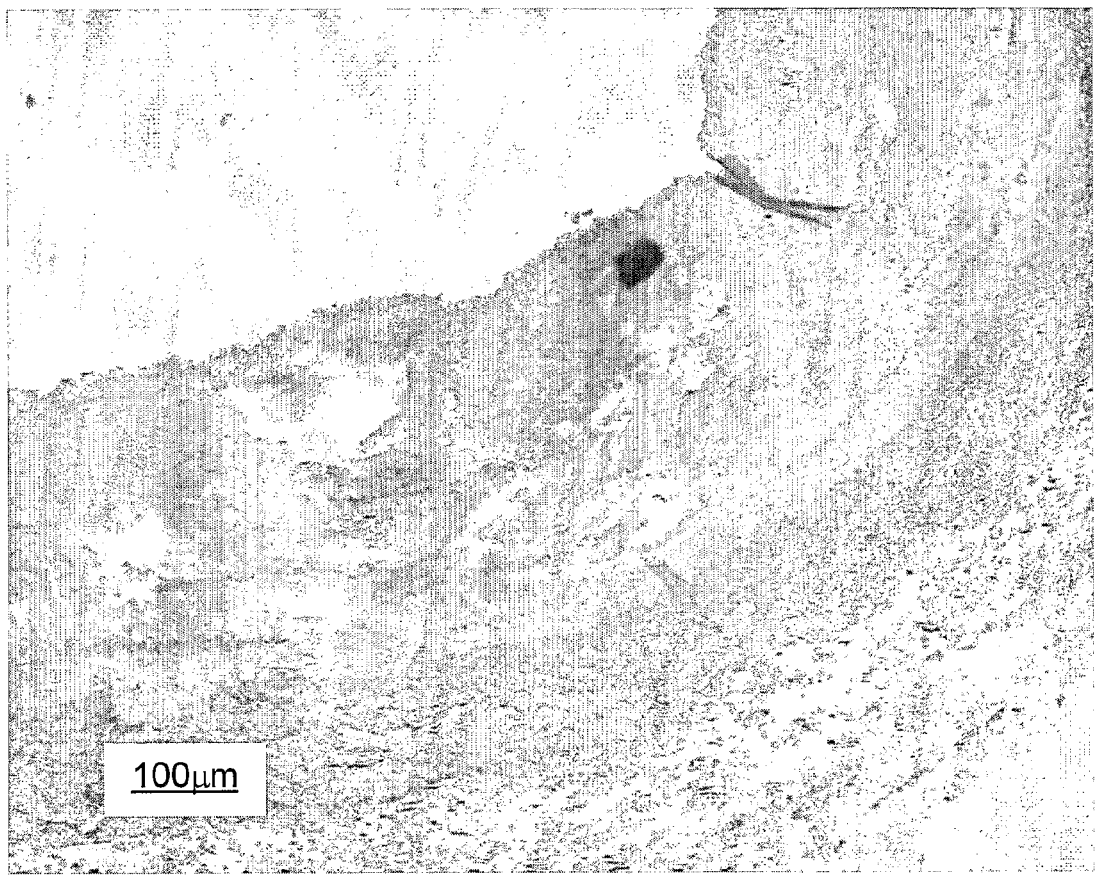
FIG. 14 shows localized damage in biological material produced by using the method of the invention to produce cavitation effects only.

The results of an experiment designed to show the feasibility of producing localized damage in biological material by using the method of the invention to produce cavitation effects only is shown in FIG. 14. In the figure is shown a cross-section of a small area of an artery after the waveform of FIG. 5 was focused in this area. The light area in the upper left is the hollow center of the artery through which the blood flows. The lower right is the edge of the arterial wall. The endothelial layer is totally absent as a result of the procedure. Areas of considerable damage can also be seen in the tunica media layer, where the organized smooth muscle fibers are destroyed in multiple locations.

The above experiments, as well as many others allow the following conclusions to be drawn about the invention:

Generation of localized damage by cavitation only can be produced by the method and system of the invention.

The localized generation of cavitation can also be used for producing efficient hyperthermia, for ablation or coagulation of tissue. The two-stage process is more effective than either cavitation or heating alone and includes a first step of bubble creation by cavitation followed by a second step of thermal heating.

The apparatus and method of the invention enable visualization of the location of the production of bubbles and allow a decision to be made whether to continue with the treatment, to discontinue it, or to change its location.

A gradual temperature increase in temperature occurs at the focal point, while several millimeters away no temperature changes are observed. This result was revealed when thermocouples were used to measure the temperature, thereby verifying the procedure.

Changes in the power level during cavitation affect the temperature increase and the bubbles production, but have little effect on the duration of the treatment; i.e. increasing the power level leads to increased bubble production and increased temperature.

A limitation to the use of to high power levels is that if too many bubbles are produced they are difficult to control and damage might be caused outside of the intended treatment volume.

The results show that a change in heating time affects not only the temperature increase but also the duration of the treatment. But it does not affect the production of bubbles during the heating stage; i.e. the heating region can be contained within the region marked during the cavitation period.

Figure 15A:
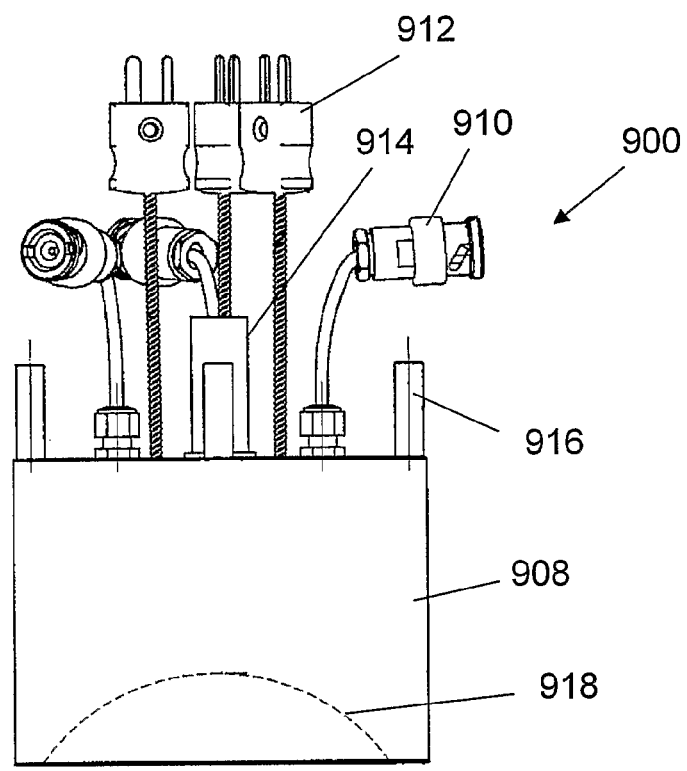
FIGS. 15A to 15D show an embodiment of a transducer array comprising annular transducers.
Figure 15B:
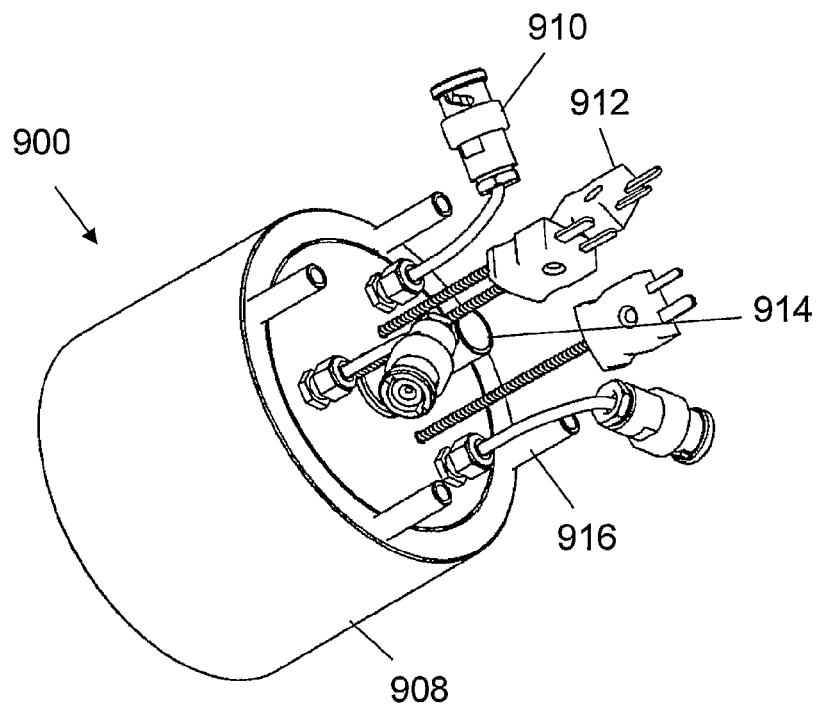

Another embodiment of a transducer array that can be used to carry out the method of the invention is shown in FIGS. 15A to 15D. FIG. 15A is a side view and FIG. 15B a perspective view showing the features of the outside of cylindrical holder 908 of array 900. Shown in these figures are three connectors 910 for the power cables to the three transducers and three connectors 912 for thermocouples. The thermocouples in array 900 are placed on the rear sides of each of the transducers to monitor their performance during the development stage of the array. They are not necessary features of a commercial array. Also shown on the top of holder 908 is air inlet 914 and air outlets 916, which are provided to pass air over the backs of the transducers and remove heat from the inside of holder 908.

As opposed to the array 300 shown in FIGS. 3A and 3B, which comprises cylindrical transducers 206, the array 900 is comprised of three annular transducers 902, 904, and 906. The three transducers are arranged such that their front faces form a spherical shaped active area 918, which focuses the energy from all of the transducers at the same point below the bottom of the holder. The common focal point (f in FIG. 5C) is located on the vertical symmetry of holder 908 and is the center of curvature of spherical active area 918.

Figure 15C:
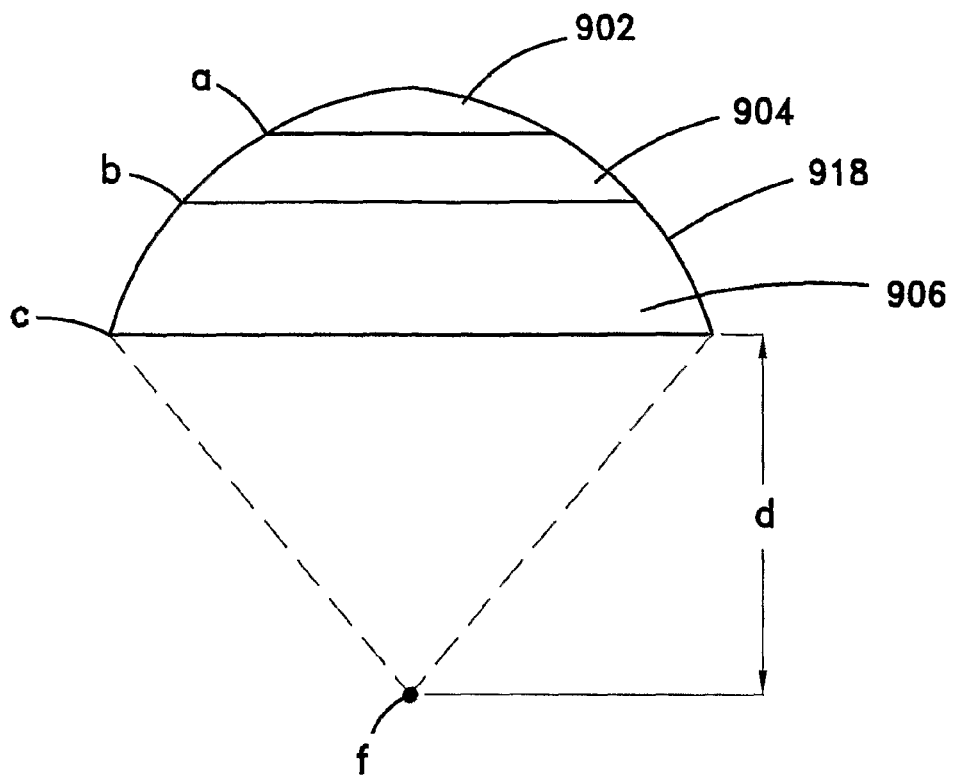
Figure 15D:
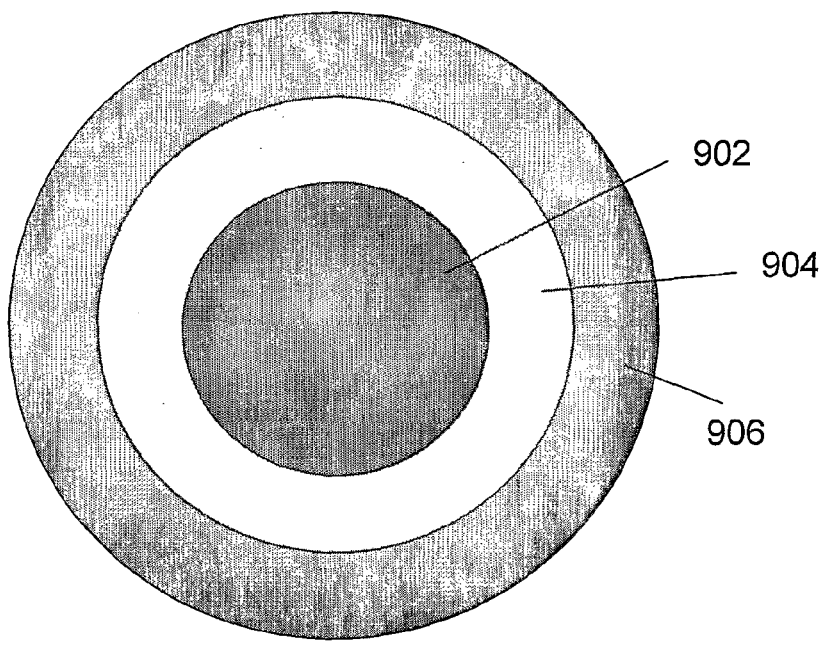

FIG. 15C is a cross-sectional view showing the arrangement of the three transducers. Lines a, b, and c are respectively the bottom edges of transducers 902, 904, and 906. The bottom of transducer 902 and the inner side surfaces of transducers 904 and 906 define the spherical active surface 918. Line c also represents the bottom edge of holder 908 and therefore the "skin plane", when the array is placed on a patient's body during a therapeutic procedure. The distance from the skin plane to the focus f is designated by the letter d. FIG. 15D is a view from the bottom of the array showing the location of transducers 902, 904, and 906 on the active surface 918.

An illustrative, but nor limitative, example of the dimensions of an array 900 designed for therapeutic treatment of veins is: height and diameter of holder 908 are 65 mm and 88 mm respectively; radius of curvature of the spherical active surface 918 is 45 mm; and distance d is 27 mm. The frequencies of the transducers in the array are 350 KHZ, 700 KHZ, and 1050 KHZ. It is to be noted that the ratio of these frequencies is 1:2:3. This is different from the ratio 1:2:4 of array 300, which was described hereinabove and used in the above described experiments. This illustrates that the invention is not limited to any particular frequencies or for that matter to using three transducers. The main consideration in choosing the number, frequencies, and other parameters of the transducers and other components of the system is the waveform of the signal that is to be produced by the array in order to achieve the intended results.

The invention can be used for a variety of non-invasive (or minimally invasive) procedures designed to provide localized treatment or damage to cells and tissue. The treatment provided is based on the mechanism of production of microbubbles and cavitation effects, on the mechanism of hyperthermia based on the existence of the microbubbles, or on a combination of both mechanisms. The procedures are operational under guidance and control of ultrasound imaging (or other imaging modality), and can also be operated without such guidance and control, by using preset parameters. The procedures are of short duration. A typical two-stage procedure comprises a cavitation stage taking e.g. 10-30 sec followed by a heating stage taking e.g. 30-90 sec. The procedure must be repeated when larger regions need to be treated.

A nonlimitative list of medical procedures that can be carried out using the method and apparatus of the invention is:

Occlusion of varicose veins. The procedure is based on using ultrasound waves, generated according to the method of the invention, to initiate scaring and closure of the varicose vein. The invention allows a non-invasive procedure for office-based physicians and can be used for both diagnostic and therapeutic procedures. The method is not limited by vein structure or width. Therapy and image monitoring can be performed simultaneously and using the same probe and therefore additional expensive accessories are not required.

The preferred embodiment of the varicose vein treatment procedure makes use of cavitation damage only and thereby limits the discomfort and scarring that often results from laser treatment or treatment based on high intensity focused ultrasound (HIFU). In situations in which cavitation damage alone will not produce the desired results, the two-stage procedure described hereinabove is employed in which, after a short period of bubble formation and cavitation, the waveform is changed to produce rapid hyperthermia. A third alternative is to use the heating waveform alone, without the preliminary stage of bubble formation, to cause hyperthermia. The method of the invention has several advantages over the prior art. The most important of which is the efficiency with which the bubble cloud aids the absorption of the heat. This allows the use of lower intensity beams and shorter exposure times than in conventional HIFU treatments. Equally important is the ability to limit the treated region to a very small volume located within the vein thereby limiting the damage to nearby tissues and organs. This latter advantage follows from the facts that in the method of the present invention the ultrasound energy is highly focused, the specific waveform causing the cavitation is limited to a specific volume within the focused region, and the formation of bubbles has higher likelihood to take place in liquid than in tissue. For example, in the above mentioned U.S. Pat. No. 6,436,061, no bubble cloud is present. This is believed to make control of the application of the focused ultrasound difficult since the blood, in which the beam is focused, is a much poorer absorber than the surrounding tissue. The present invention is based on an entirely different mechanism for treatment of varicose veins than HIFU. In HIFU absorption of ultrasound energy by tissue or blood constituents is required. According to the preferred embodiment of the present invention, the treatment is based on a mechanism of bubble formation produced only by local pressure changes.

Activation of cellular (e.g. endothelial cell) processes in the body, by either localized pressure forces or shear forces that produce therapeutic responses or damage. For example, localized drug delivery, gene therapy and angiogenesis.

Therapy of cancerous tissue by cavitation damage and/or rapid hyperthermia, resulting in apoptosis, tissue ablation or necrosis.

Therapy of cancerous tissue by damage and closure of the supply and drainage vasculature by cavitation, and/or rapid hyperthermia via coagulation of the arteries supplying the tumor.

Ablation of ectopic foci or re-entry loops within the cardiac walls, mainly within the ventricular walls.

Thrombolysis of clotted or semi-clotted arteries, e.g. coronary arteries, the carotid arteries, cerebral arteries, peripheral arteries etc.

Lipolysis or other methods of disintegration of fat cells, either by the mechanism of microbubbles collapse and/or by hyperthermia, resulting in apoptosis and drainage of fat deposits.

Coagulation of internal bleedings within the body.

Non-invasive surgery of internal tissues and organs, by disintegration of cells along the cut, with possible visualization and control via the generated microbubbles.

Although the invention has been presented in relation to the medical procedures that can be performed using it, skilled persons will readily understand that the method and system of the invention can easily and advantageously be adapted mutatis mutandis to numerous applications in industry and commerce, e.g. for ultrasonic cleaning.

It also is to be noted that in certain situations, wherein a sufficient population of microbubbles cannot be generated in situ, contrast agents can be introduced into the focal zone to increase the efficiency of the adsorption of energy from the heating waveform.

Although embodiments of the invention have been described by way of illustration, it will be understood that the invention may be carried out with many variations, modifications, and adaptations, without departing from its spirit or exceeding the scope of the claims.

The invention claimed is:

1. A method of using ultrasound waves focused at a specific location in a medium to cause localized production of microbubbles at said location, to control said production, and to control cavitational and heating effects that take place at said location, the method comprising:
   providing multiple ultrasonic transducers;
   focusing the transducers at said location;
   simultaneously directing ultrasound waves from the transducers at said location; and
   selecting a range of parameters of the ultrasound waves being directed from the multiple ultrasonic transducers focused at said location in order to induce cavitation, and to produce from interference of the ultrasound waves at said location a combined waveform:
   wherein said combined waveform comprising a spatial and/or temporal combination of two waveforms—one waveform comprising high negative peaks and small positive peaks and the second waveform comprising high positive peaks and only small negative peaks, said combined waveform allowing control of size distribution of the microbubbles and temporal changes of the distribution.

2. The method according to claim 1, wherein the combined waveform encouraging the production of heat comprises one of:
   a waveform comprising high positive peaks and only small negative peaks; and
   a sinusoidal waveform.

3. A method according to claim 2, wherein the combined waveform comprising high positive peaks and small negative peaks encourages reduction of the size of said microbubbles.

4. A method according to claim 1, wherein a number of the transducers is three.

5. A method according to claim 1, wherein a radius of the microbubbles is in a range from a fraction of a micron up to 100.

6. The method according to claim 1, further comprising the step of measuring changes in tissue or microbubble size and accordingly adjusting the waveform to include more negative peaks, more positive peaks, or more equal sized waves.

7. The method according to claim 1, further comprising the step of measuring temperature of the medium and modifying an output of the transducers according to the measured temperature.

8. The method according to claim 1, further comprising the step of monitoring generation of the microbubbles at the specific location by using an ultrasound imaging or non-imaging system and controlling the system for one or more of the following purposes:
   so that a number of microbubbles will be as planned;
   for aiming a focused beam to the targeted location; and
   to re-align the beam to a different location.

9. A method according to claim 8, wherein a response at a half harmonic or at higher harmonics of the transmitted frequencies is used by the ultrasound imaging or non-imaging system to measure one or more of the following:
   effect of the heating;
   duration of said effect;
   number of microbubbles generated within the targeted region; and
   spatial distribution of said microbubbles generated within said targeted region.

10. A method according to claim 1, wherein the multiple ultrasonic transducers are arranged as an array, designed so that their mechanical focus and their own focus combine at a same point in space.

11. A method according to claim 10, wherein the point in space can be moved by either shifting the whole array, by repositioning of individual transducers, or by phase shift of an excitation pulse.

12. A method according to claim 10, wherein the ultrasound waves transmitted by the multiple ultrasonic transducers are designed to produce by interference specific waveforms at a focal point, which are not produced at other locations.

13. A method according to claim 12, wherein the specific waveforms can be modified to produce one of the following effects:
   cause cavitation with no significant change in temperature;
   increase the temperature with minimal cavitation;
   suppress cavitation; and
   a combination of these effects.

14. A method according to claim 12, wherein a region within a focal zone of all the transducers in which the specific waveform develops at significant intensities and amplitudes of the waveforms are less than −3 DB of a maximum amplitude at a distance less than 1 mm away from a point of said maximum amplitude in lateral directions and less than 1.5 mm away in axial directions.

15. A method according to claim 1, wherein localized production of microbubbles at the location and control of the cavitational and heating effects that take place at said location are for therapeutic purposes.

16. A method according to claim 15, wherein the therapy is at least one of:
   occlusion of varicose veins and telangiectasia;
   activation of cellular processes in a body, by either localized pressure forces or shear forces that produce therapeutic responses or damage;

therapy of cancerous tissue by cavitation damage and/or rapid hyperthermia, resulting in apoptosis, tissue ablation or necrosis;

therapy of cancerous tissue by damage and closure of supply and drainage vasculature by cavitation, and/or rapid hyperthermia via coagulation of arteries supplying a tumor;

ablation of ectopic foci or re-entry loops within cardiac walls, mainly within ventricular walls;

thrombolysis of clotted or semi-clotted arteries, lipolysis or other methods of disintegration of fat cells, either by a mechanism of microbubbles collapse and/or by hyperthermia, resulting in apoptosis and drainage of fat deposits;

coagulation of internal bleedings within the body; and non-invasive surgery of internal tissues and organs, by disintegration of cells along a cut.

17. A method according to claim 16, wherein activation of cellular processes in the body produces therapeutic responses or damage, including at least one of:
localized drug delivery,
gene therapy, and
angiogenesis.

18. A method according to claim 16, wherein thrombolysis of clotted or semi-clotted arteries is performed in arteries chosen from at least one of:
coronary arteries,
carotid arteries,
cerebral arteries, and
peripheral arteries.

19. A method according to claim 1, wherein the transducers are placed extra-corporally, in close proximity to an organ to be treated, with ultrasound gel or water surrounding the ultrasound transducers and space between it and the organ.

20. A method of occluding varicose veins comprising the steps of:
a) focusing multiple transducers at a same location within a vein;
b) selecting a range of parameters of said multiple transducers to produce a waveform comprising high negative peaks and small positive peaks, said waveform encouraging creation of a cloud of microbubbles;
c) continuing production of the waveform until cavitation causes destruction of cells and initiation of scaring of tissue at said location;
d) focusing said transducers at another location within said vein; and
e) repeating steps (b), (c) and (d) until enough scaring has been initiated to cause occlusion of said vein.

21. A method according to claim 20, wherein two additional steps are added between steps (c) and (d), said additional steps comprising:
f) changing the range of parameters of the multiple transducers to produce a heating waveforms, said waveform encouraging production of heat at the location; and
g) continuing the production of the waveform until the heating causes destruction of cells and initiation of scaring of the tissue at said location.

22. A system comprising:
at least three arbitrary waveform signal generators;
at least three or more wide-band power amplifiers coupled to the waveform signal generators; wherein
three transducers coupled to the wide-band power amplifiers and configured to focus ultrasound waves at a location in a medium to cause localized production of microbubbles at said location; and
at least one workstation configured to control the production of the microbubbles at said location, and cavitational and heating effects that take place at said location, wherein the workstation selects a range of parameters of the ultrasound waves being directed from the transducers focused at said location in order to induce cavitation, and to produce from interference of the ultrasound waves at said location:
a combined waveform comprising a spatial and/or temporal combination of two waveforms, one waveform comprising high negative peaks and small positive peaks and a second waveform comprising high positive peaks and small negative peaks, said combined waveform allowing control of size distribution of the microbubbles and temporal changes of the distribution.

23. A system according to claim 22, wherein the three transducers are arranged as an array, designed so that their mechanical focus and their own focus combine at a same point in space.

24. A system according to claim 23, wherein the point in space can be moved by either shifting the whole array, by repositioning of individual transducers, or by phase shift of an excitation pulse.

25. A system according to claim 23, wherein the ultrasound waves transmitted by the three transducers are designed to produce by interference specific waveforms at a focal point, which are not produced at other locations.

26. A system according to claim 25, wherein the specific waveforms can be modified to produce one of the following effects:
cause cavitation with no significant change in temperature;
increase the temperature with minimal cavitation;
suppress cavitation; and
a combination of these effects.

27. A system according to claim 25, wherein a region within a focal zone of all the transducers in which the specific waveform develops at significant intensities and amplitudes of the waveforms are less than −3 DB of a maximum amplitude at a distance less than 1 mm away from a point of said maximum amplitude in lateral directions and less than 1.5 mm away in axial directions.

28. A system according to claim 23, adapted for use in a therapeutic procedure;
wherein the array is placed extra-corporally, in close proximity to an organ to be treated, with ultrasound gel or water surrounding the ultrasound transducers and the space between it and the organ.

29. A system according to claim 28, wherein the therapeutic procedure is at least one of:
occlusion of varicose veins and telangiectasia;
activation of cellular processes in the body, by either localized pressure forces or shear forces that produce therapeutic responses or damage;
therapy of cancerous tissue by cavitation damage and/or rapid hyperthermia, resulting in apoptosis, tissue ablation or necrosis;
therapy of cancerous tissue by damage and closure of the supply and drainage vasculature by cavitation, and/or rapid hyperthermia via coagulation of the arteries supplying the tumor;
ablation of ectopic foci or re-entry loops within the cardiac walls, mainly within the ventricular walls;
thrombolysis of clotted or semi-clotted arteries, lipolysis or other methods of disintegration of fat cells, either by the mechanism of microbubbles collapse and/or by hyperthermia, resulting in apoptosis and drainage of fat deposits;

coagulation of internal bleedings within the body; and
non-invasive surgery of internal tissues and organs, by disintegration of cells along the cut.

30. A system according to claim 22, further comprising an ultrasound imaging or non-imaging system and a control box.

31. A system according to claim 30 further comprising the ultrasound imaging or non-imaging system configured to view and monitor the region being targeted, monitors generation of the microbubbles at the desired location, and controls the system for one or more of the following purposes:

so that the number of microbubbles will be as planned;
for aiming the focused beam to the targeted location; and
to re-align the beam to a different location.

32. A system according to claim 30, wherein a response at the half harmonic or at higher harmonics of the transmitted frequencies is used by the ultrasound imaging or non-imaging system to measure one or more of the following:

the effect of the heating;
the duration of said effect;
the number of microbubbles generated within the targeted region; and
the spatial distribution of said microbubbles generated within said targeted region.

33. A system according to claim 30, wherein the ultrasound imaging or non-imaging system is controlled by the workstation to which it is connected through the control box.

34. A system according to claim 30, wherein the ultrasound imaging or non-imaging system measures the changes in tissue or the microbubbles size and the control box and workstation accordingly adjust the waveform to include more negative peaks, positive peaks or equal sized waves.

35. A system according to claim 22, further comprising a temperature measurement system.

36. A system according to claim 35, wherein the temperature measurement system comprises one or more thermocouples.

37. A system according to claim 35, wherein the temperature measurement system configured to modify the output of the transducers according to the measured temperature.

* * * * *